United States Patent [19]
Rey-Senelonge et al.

[11] Patent Number: 5,266,489
[45] Date of Patent: Nov. 30, 1993

[54] RECOMBINANT HERPESVIRUSES, IN PARTICULAR FOR THE PRODUCTION OF VACCINES, PROCESS FOR PREPARING THEM, PLASMIDS PRODUCED DURING THIS PROCESS AND VACCINES OBTAINED

[75] Inventors: Arielle Rey-Senelonge; Gilla Kohen, both of Rillieux la Pape, France

[73] Assignee: Rhone Merieux, France

[21] Appl. No.: 778,890

[22] PCT Filed: Mar. 7, 1991

[86] PCT No.: PCT/FR91/00184
§ 371 Date: Jan. 3, 1992
§ 102(e) Date: Jan. 3, 1992

[87] PCT Pub. No.: WO91/13995
PCT Pub. Date: Sep. 19, 1991

[30] Foreign Application Priority Data
Mar. 12, 1990 [FR] France .................. 90 03105

[51] Int. Cl.$^5$ .................. C12N 15/85; A61K 39/245
[52] U.S. Cl. .................. 435/320.1; 435/69.1; 435/235.1; 435/172.3; 435/69.3; 536/23.72; 424/93 A
[58] Field of Search .................. 435/235.1, 69.1, 320.1; 424/93 A; 536/27, 23.72

[56] References Cited
PUBLICATIONS

Shih et al., PNAS, vol. 81, 1984, pp. 5867-5870.
J. McLauchlan, J. B. Clements, DNA sequence homology between two co-linear loci on the HSV genome which have different transforming abilities, The Embo Journal, 2, (11), 1953-1961 (1983).
J. McLauchlan, J. B. Clements, Organization of the Herpes Simplex Virus Type 1 Transcription Unit Encoding Two Early Proteins with Molecular Weights of 140,000 and 40,000, J. Gen. Virol., 64, 997-1006 (1983).
S. Simpson, J. McLauchlan, J. B. Clements, 14th International Herpesvirus Workshop, Nyborg-strand, Denmark (1989).
M. A. Swain, D. A. Galloway, Herpes Simplex Virus specifies Two Subunits of Ribonucleotide Reductase Encoded by 3'-Coterminal Transcripts, J. Virol., 57, (3), 802-808 (1986).
D. J. Goldstein, S. K. Weller, Herpes Simplex Virus Type 1-Induced Ribonucleotide Reductase Activity is Dispensable for Virus Growth and DNA Synthesis: Isolation and Characterization of an ICP6 lacZ Insertion Mutant, Virology, 62, 196-205 (1988).
D. J. Goldstein, S. K. Weller, Factor(s) Present in Herpes ..., Virology, 166, 41-51 (1988).
V. G. Preston, A. J. Darling, I. M. McDougall, The Herpes Simplex Virus Type 1 ..., Virology, 167, 458-467 (1988).
J. G. Jacobson, D. A. Leib, D. J. Goldstein, C. L. Bogart, P. A. Schaffer, S. K. Weller, D. M. Coen, A Herpes Simplex Virus Ribonucleotide ..., Virology, 173 (1), 276-283 (1989).

Primary Examiner—Richard A. Schwartz
Assistant Examiner—David Guzo
Attorney, Agent, or Firm—Larson and Taylor

[57] ABSTRACT

The recombinant virus chosen from the turkey herpesvirus(HVT), Aujeszky's disease virus (PRV), infectious bovine rhinotracheitis virus (BHV) feline infectious rhinotracheitis virus (FHV), equine rhinopneumonia virus (EHV), canine herpesvirus (CHV), duck herpesvirus, human simplex herpesvirus (HSV), varicella virus (VZV), Epstein-Barr virus (EBV), cytomegalovirus (CMV), comprises at least one heterologous gene, coding particularily for a viral, bacterial or parasitic immunogen inserted in the region of the genome of the said virus corresponding to the gene of the small sub-unit RR2 of ribonucleotide reductase so that it may be expressed. The method for preparing a virus of this type involves inserting the heterlogous gene into the said region of the genome, particularly after partial or total deletion of this region. The recombiant virus obtained may be used particularly for preparing living vaccines. The small sub-unit of the ribonucleotide reductase of the turkey herpesvirus (HVT) has been sequenced.

17 Claims, 6 Drawing Sheets

SEQUENCE LISTING ( 1 ) GENERAL INFORMATION:

( i i i ) NUMBER OF SEQUENCES:7

( 2 ) INFORMATION FOR SEQ ID NO:1:

( i ) SEQUENCE CHARACTERISTICS:
        ( A ) LENGTH:3278 base pairs
        ( B ) TYPE:nucleic acid
        ( C ) STRANDEDNESS:double
        ( D ) TOPOLOGY:circular ( i i ) MOLECULE TYPE:genomic DNA ( i i i ) HYPOTHETICAL:yes ( i v ) ANTI-SENSE:no ( v i ) ORIGINAL SOURCE:
        ( A ) ORGANISM:Turkey herpes virus(HVT)
        ( B ) STRAIN:FC126
        ( C ) INDIVIDUAL ISOLATE:turkey ( v i i ) IMMEDIATE SOURCE:
        ( A ) LIBRARY:plasmid
        ( B ) CLONE:pHVT K1

( i x ) FEATURE:
        ( A ) NAME/KEY:ribonucleotid reductase gene
        ( B ) LOCATION: from to description
          1 1662 RR1 gene
          1695 2759 RR2 gene ( x i ) SEQUENCE DESCRIPTION:SEQ ID NO:1:

```
GAT  CCA  AGA  ACT  ACA  ACC  ACC  CAA  GAT  ACT  ATC  AAA  GTT  ATA  ACG        45
Asp  Pro  Arg  Thr  Thr  Thr  Thr  Gln  Asp  Thr  Ile  Lys  Val  Ile  Thr
```

```
                                         -continued 1                    5                    10                   15
AAT GAT GTT GTT CCC CAT CTC CTG GCA CGA GGA GGG ATA GGC ATA                  90
Asn Asp Val Val Pro His Leu Leu Ala Arg Gly Gly Ile Gly Ile
 20              25                  30

TCA TTG CAG CAC GTC AAT CAA AAA TCG GGT CTG ATG CAT GTT TTA                 135
Ser Leu Gln His Val Asn Gln Lys Ser Gly Leu Met His Val Leu
 35              40                  45

AAG CTG ATA GAT TCA TTG ATT GTG GCC ACT AAT GTG AAC GAG TCC                 180
Lys Leu Ile Asp Ser Leu Ile Val Ala Thr Asn Val Asn Glu Ser
 50              55                  60

CGG CCG ACG GGC GTT TGT GTG TAT TTG GAA CCC TGG CAT TCA GAC                 225
Arg Pro Thr Gly Val Cys Val Tyr Leu Glu Pro Trp His Ser Asp
 65              70                  75

ATC ATG TCG GCT TTG ACG ATG CGC GGA ATG ATG GCC GCC GAG GAA                 270
Ile Met Ser Ala Leu Thr Met Arg Gly Met Met Ala Ala Glu Glu
 80              85                  90

TCG AGA AGA TGT GAT AAT GTA TTC CTA GCT CTT TGG GCG TGC GAC                 315
Ser Arg Arg Cys Asp Asn Val Phe Leu Ala Leu Trp Ala Cys Asp
 95             100                 105

CTC CTG TTT AAG AGA TAC CTG CGA TAT GTT AAT GGA GAA AAA AAT                 360
Leu Leu Phe Lys Arg Tyr Leu Arg Tyr Val Asn Gly Glu Lys Asn
110             115                 120

GTG ATG TGG ACT TTA TTT GAC TCC CGC GCG TCT ATT TTA TCA AAA                 405
Val Met Trp Thr Leu Phe Asp Ser Arg Ala Ser Ile Leu Ser Lys
125             130                 135

CTA TAT GGC GAT AAA TTC GAG GTG GAA TAT GAA CGT CTC GAA AAA                 450
Leu Tyr Gly Asp Lys Phe Glu Val Glu Tyr Glu Arg Leu Glu Lys
140             145                 150

GAA GGT ATT GGG GTG GCC CAA ATT CCA ATC AGA GAC ATG ATG TTT                 495
Glu Gly Ile Gly Val Ala Gln Ile Pro Ile Arg Asp Met Met Phe
155             160                 165

GCG ATC ATA AAA AGC GCA GCT TCT ACT GGA AGT CCA TTC ATT CTC                 540
Ala Ile Ile Lys Ser Ala Ala Ser Thr Gly Ser Pro Phe Ile Leu
170             175                 180

TTC AAA GAC GCC TGC AAC CGA CAT TAC ATC ACG GAC ACC CAG GGC                 585
Phe Lys Asp Ala Cys Asn Arg His Tyr Ile Thr Asp Thr Gln Gly
185             190                 195

GAT GCT ATT GCG GGA TCC AAT CTG TGC ACA GAA ATA ATA CAG AAA                 630
Asp Ala Ile Ala Gly Ser Asn Leu Cys Thr Glu Ile Ile Gln Lys
200             205                 210

ACA AAC GAA TCC ACA AAT GGC GTG TGC ACC CTA GCA AGC ATT AAT                 675
Thr Asn Glu Ser Thr Asn Gly Val Cys Thr Leu Ala Ser Ile Asn
215             220                 225

CTG GCC AGA TGC GTT CGC CGT GTT AAC GTG AAT GTA AAT TCG ATT                 720
Leu Ala Arg Cys Val Arg Arg Val Asn Val Asn Val Asn Ser Ile
230             235                 240

TTG ATG CCC TTA GGC ATG CCG TTT CGA CTG GCC ACC GTT TTT ACC                 765
Leu Met Pro Leu Gly Met Pro Phe Arg Leu Ala Thr Val Phe Thr
245             250                 255

AAT GCA ATA ATG GAT GGG AGT GAT GTC CCC ACA GTC AAA TCT CAA                 810
Asn Ala Ile Met Asp Gly Ser Asp Val Pro Thr Val Lys Ser Gln
260             265                 270

TCG GGT CGA GAC CGC AAC AGA TCT ATT GGT ATA GGC GTC CAA GGA                 855
Ser Gly Arg Asp Arg Asn Arg Ser Ile Gly Ile Gly Val Gln Gly
275             280                 285

TTT CAT ACA GCC ATG CTA TCT TTG GGT CTA GAT TTA GAG GAC GGA                 900
Phe His Thr Ala Met Leu Ser Leu Gly Leu Asp Leu Glu Asp Gly
290             295                 300

GCT GTC AGA GCA CTT AAT AAG CAA ATA TTT GAA CTA ATG CTA TTA                 945
Ala Val Arg Ala Leu Asn Lys Gln Ile Phe Glu Leu Met Leu Leu
305             310                 315
```

```
GAA GCT ATG ACC GTG AGC TGC GAA TTT TGT GAG CGG GGT CTT CCA                         990
Glu Ala Met Thr Val Ser Cys Glu Phe Cys Glu Arg Gly Leu Pro
320             325             330

CCG TTC CCA GAC TTC TCT GAC AGC TAC TAT GCT CAA GGC CGT TTG                        1035
Pro Phe Pro Asp Phe Ser Asp Ser Tyr Tyr Ala Gln Gly Arg Leu
335             340             345

CAT TTT GAT GGA TGG GAT AGT GTG GAG TTA ACG GCC CCC GAG GAA                        1080
His Phe Asp Gly Trp Asp Ser Val Glu Leu Thr Ala Pro Glu Glu
350             355             360

TGG GGA GTT CTC CGC GGT CGT ATA ATG TCG TCT GGG CTT TAC AAC                        1125
Trp Gly Val Leu Arg Gly Arg Ile Met Ser Ser Gly Leu Tyr Asn
365             370             375

GCC CAG TTC ATA GCG CTG ATG CCT ACT GCC GCA TCG GCG CAA GTG                        1170
Ala Gln Phe Ile Ala Leu Met Pro Thr Ala Ala Ser Ala Gln Val
380             385             390

ACC GAG GTT AGC GAA GGA TTT GCC CCT TTG TTC AGT AAC ATG TTC                        1215
Thr Glu Val Ser Glu Gly Phe Ala Pro Leu Phe Ser Asn Met Phe
395             400             405

AGC AAG GTG ACA AGT GCC GGG GAA CTG CTT AGA CCC AAC AGT CAA                        1260
Ser Lys Val Thr Ser Ala Gly Glu Leu Leu Arg Pro Asn Ser Gln
410             415             420

TTA ATG CGG GAC GTG AGA CAG ATA TAT CCC GAT AAT GAG CAG CGT                        1305
Leu Met Arg Asp Val Arg Gln Ile Tyr Pro Asp Asn Glu Gln Arg
425             430             435

CGC TTA AGC GCC ATT ACT GCA CTT GAG TCC ACT GCA TGG TGC GTC                        1350
Arg Leu Ser Ala Ile Thr Ala Leu Glu Ser Thr Ala Trp Cys Val
440             445             450

AAA GAA GCG CTA GGG GAT CGG CCG GAA TGT ACT CGT CTA CTC AAA                        1395
Lys Glu Ala Leu Gly Asp Arg Pro Glu Cys Thr Arg Leu Leu Lys
455             460             465

TAT AAA ACG GCG TTC GAA TAC GAT CAA TCT CTC CTA ATA GAT TTA                        1440
Tyr Lys Thr Ala Phe Glu Tyr Asp Gln Ser Leu Leu Ile Asp Leu
470             475             480

TGT GCG GAT AGA GCC CCT TTT GTG GAT CAG AGC CAA TCA ATG ACT                        1485
Cys Ala Asp Arg Ala Pro Phe Val Asp Gln Ser Gln Ser Met Thr
485             490             495

CTG TTT GTA ACG GAA ACA GCT GAC GGC ACG CTA TTG GCA TCC CGC                        1530
Leu Phe Val Thr Glu Thr Ala Asp Gly Thr Leu Leu Ala Ser Arg
500             505             510

GTC ATG AAG CTC TTA CAT GCC TAT AAA AGC TGG TCT CAA AAC GGG                        1575
Val Met Lys Leu Leu His Ala Tyr Lys Ser Trp Ser Gln Asn Gly
515             520             525

AAT GTA CTA TTG CAA GAT CGC AAG GCT ACG AAT ACT GGC ATA TTT                        1620
Asn Val Leu Leu Gln Asp Arg Lys Ala Thr Asn Thr Gly Ile Phe
530             535             540

AGC GGC GAC GGA GAA CTG ACC TGT TCT TCC TGC GTG TTG    TAATAAC                     1666
Ser Gly Asp Gly Glu Leu Thr Cys Ser Ser Cys Val Leu
545             550

CAC CGTTTATTAA CTCAATATAG CCGCC    ATG AAC AAC CCA GTG CAT GCT GCC                 1718
                                   Met Asn Asn Pro Val His Ala Ala
                                   1               5

GGG AAT CCG CCG AAC AAT TAT TTT TCT TTA GAT GGG ACC GAT CTT                        1763
Gly Asn Pro Pro Asn Asn Tyr Phe Ser Leu Asp Gly Thr Asp Leu
10              15              20

CAT CTT TCC GAG AGA GGG GCC ACT TCT CCG AAA GGG AGT GAT GGG                        1808
His Leu Ser Glu Arg Gly Ala Thr Ser Pro Lys Gly Ser Asp Gly
25              30              35

GGA GAC CTA GCC TCT CCG TAC GTG AAC AAT TGC CAT ATC ACA ACG                        1853
Gly Asp Leu Ala Ser Pro Tyr Val Asn Asn Cys His Ile Thr Thr
40              45              50

GCG CAA TAT TTC TAC GTT CCG GAA TGC CCT GAT ATA GGA AAC CTA                        1898
Ala Gln Tyr Phe Tyr Val Pro Glu Cys Pro Asp Ile Gly Asn Leu
```

```
  55                          60                          65
CGA TCT TTG AGC ATC ATG AAC CGG TGG ACC GAA ACG GAA TTC GTA    1943
Arg Ser Leu Ser Ile Met Asn Arg Trp Thr Glu Thr Glu Phe Val
 70              75                  80

ATT GCA GAC GAC CTC GAG GAT GTC GGC AAG CTT AAG AAT GAA AAA    1988
Ile Ala Asp Asp Leu Glu Asp Val Gly Lys Leu Lys Asn Glu Lys
 85              90                  95

AAT TTT TAT CGC TTT CTA TTT ACC TTT TTA TCC GCC GCC GAC GAT    2033
Asn Phe Tyr Arg Phe Leu Phe Thr Phe Leu Ser Ala Ala Asp Asp
100             105                 110

CTA GTT AAC TTG AAT ATA GAC AGT CTG TTG AGT TTA TTC ACT CAG    2078
Leu Val Asn Leu Asn Ile Asp Ser Leu Leu Ser Leu Phe Thr Gln
115             120                 125

AAA GAT ATA CAT CAT TAT TAC TTT GAA CAG GAA TGT ATA GAA GCT    2123
Lys Asp Ile His His Tyr Tyr Phe Glu Gln Glu Cys Ile Glu Ala
130             135                 140

GTC CAT TCG AGG GCC TAC AGT ATA ATT CAG CTA ATG CTG TTC AGC    2168
Val His Ser Arg Ala Tyr Ser Ile Ile Gln Leu Met Leu Phe Ser
145             150                 155

AAT GAT CAA GCC GCT CGC CAA GAA TAC GTC ACC TCA ACT TTG AGA    2213
Asn Asp Gln Ala Ala Arg Gln Glu Tyr Val Thr Ser Thr Leu Arg
160             165                 170

TCC CCC GCA ATT TTA TCA AAA TTG GAA TGG TTG GAA CGG CGA GTT    2258
Ser Pro Ala Ile Leu Ser Lys Leu Glu Trp Leu Glu Arg Arg Val
175             180                 185

GCA GAA TGC ACC TCT ATC GCT GAA AAA TAT ATT CTC ATG ATT TTA    2303
Ala Glu Cys Thr Ser Ile Ala Glu Lys Tyr Ile Leu Met Ile Leu
190             195                 200

ATA GAG GGT ATA TTT TTC ACT GCG TCT TTT GCT GCA ATC GCC TAC    2348
Ile Glu Gly Ile Phe Phe Thr Ala Ser Phe Ala Ala Ile Ala Tyr
205             210                 215

CTT CGT GTC AAT AAC CTG TTT GTG GTT ACA TGT CAA ATT AAC AAC    2393
Leu Arg Val Asn Asn Leu Phe Val Val Thr Cys Gln Ile Asn Asn
220             225                 230

TTG ATT AGC AGA GAT GAA GCT ATA CAC GTG GAA GCA TCC TGT TGC    2438
Leu Ile Ser Arg Asp Glu Ala Ile His Val Glu Ala Ser Cys Cys
235             240                 245

ATT TTT AAA AAT TAT CTC GCC GGC CCC AAA CCT ACT ACT GCC CGC    2483
Ile Phe Lys Asn Tyr Leu Ala Gly Pro Lys Pro Thr Thr Ala Arg
250             255                 260

ATC CAC ACG CTG TTT AAA GAA GCC GTT ACG GTG GAA TGC GAG TTC    2528
Ile His Thr Leu Phe Lys Glu Ala Val Thr Val Glu Cys Glu Phe
265             270                 275

CTC CGC ACG GCG GCT CCT CGC ACC AGT AAT ATT ATC AAT ATT GAT    2573
Leu Arg Thr Ala Ala Pro Arg Thr Ser Asn Ile Ile Asn Ile Asp
280             285                 290

GCC ATT TGC AGC TAT GTA CGG TAC AGT GCA GAC AGG TTG TTG AGA    2618
Ala Ile Cys Ser Tyr Val Arg Tyr Ser Ala Asp Arg Leu Leu Arg
295             300                 305

GCG CTT GAT ATA CTG CCC ATT TAC GAC GAA CCC AAA CCC CCT GCT    2663
Ala Leu Asp Ile Leu Pro Ile Tyr Asp Glu Pro Lys Pro Pro Ala
310             315                 320

GAT TTC CCC CTC GTC CTC ATG TCC GCT GCA AGC AAT ACT AAC TTT    2708
Asp Phe Pro Leu Val Leu Met Ser Ala Ala Ser Asn Thr Asn Phe
325             330                 335

TTC GAG CGA CGA AAC ACC GCA TAC TCT GGA AGC GTT TCA AAT GAT    2753
Phe Glu Arg Arg Asn Thr Ala Tyr Ser Gly Ser Val Ser Asn Asp
340             345                 350

CTT     TAATTCGCAA TTGAAATTAC CCGATTCACG TGTACTTTAG GTCAAATATA AAGTT  2811
Leu

CGTGT AATGCATCCT CGTTCGCGTT TCTTTTTTAG GCGACCCTAT TCCAATACTT TGTCA   2871
```

-continued

```
ACCAC TCTATTGAAG GCGTATCTCG ATGCGTCGTA AAAAGCGGAT GCTAAACTGC CCGCT     2931

TCGTT ACTATCAACT ATACTACGGA GGACCAAGTT CTCAATTGCA GAATCATCCC GCGTC     2991

TCTTG CGTAATAGGA AACCGCTTTA AGATACTGAC TCTGTGTGTT CTTCGTTCTG GTGTT     3051

ATATT TTCTATTACA TGTTTTATAA ATTTATATTC TAGAACTTCA CATTTGGTTC GGTGG     3111

AGCTC GTAAATGCGT TAACGCCTGC CGTGCGTCGC GTATTATATT TACATCGTTA TAGGT     3171

GGCGC ACAGGCGGTC TGTGCTGGAG TTATGATCAT TTTTGCGGTT CTCGCTAAA GTTGT      3231

CCGTA GATTATGCTT CAGTCCAGAC CTATCTATAT GCTTCTCGTT TA                   3278
```

(2) INFORMATION FOR SEQ ID NO:2:

(i) SEQUENCE CHARACTERISTICS:
        (A) LENGTH:2176 base pairs
        (B) TYPE:nucleic acid
        (C) STRANDEDNESS:double
        (D) TOPOLOGY:circular (ii) MOLECULE TYPE:cDNA to genomic RNA (iii) HYPOTHETICAL:yes (iv) ANTI-SENSE:no (vi) ORIGINAL SOURCE:
        (A) ORGANISM:Newcastle disease virus(NDV)
        (B) STRAIN:Texas strain
        (C) INDIVIDUAL ISOLATE:chicken (vii) IMMEDIATE SOURCE:
        (A) LIBRARY:plasmid
        (B) CLONE:pNDV 108

(ix) FEATURE:
        (A) NAME/KEY:part of matrix protein gene and fusion protein ge
        (B) LOCATION: from to description
            1 271 matrix protein gene
            431 2092 fusion protein gene (xi) SEQUENCE DESCRIPTION:SEQ ID NO:2:

```
A   CCT TCC GTG CTC GTG AAG GCG AGA GGT GCA CGG ACT AGG CTG             43
    Pro Ser Val Leu Val Lys Ala Arg Gly Ala Arg Thr Arg Leu
    1           5                   10

CTG GCA CCT TTC TTC TCT AGC AGT GGG ACA GCC TGC TAT CCT ATA            88
Leu Ala Pro Phe Phe Ser Ser Ser Gly Thr Ala Cys Tyr Pro Ile
15                  20                  25

GCA AAT GCC TCT CCT CAG GTA GCT AAG ATA CTC TGG AGT CAA ACT            133
Ala Asn Ala Ser Pro Gln Val Ala Lys Ile Leu Trp Ser Gln Thr
30                  35                  40

GCG CGC CTG CGG AGT GTA AAA ATC ATC ATT CAA GCG GGC ACC CAA            178
Ala Arg Leu Arg Ser Val Lys Ile Ile Ile Gln Ala Gly Thr Gln
45                  50                  55

CGC GCT GTC GCA GTG ACT GCT GAC CAT GAG GTT ACC TCT ACT AAG            223
Arg Ala Val Ala Val Thr Ala Asp His Glu Val Thr Ser Thr Lys
60                  65                  70

ATA GAG AAG AGG CAT ACC ATT GCT AAA TAC AAT CCT TTC AAG AAA            268
Ile Glu Lys Arg His Thr Ile Ala Lys Tyr Asn Pro Phe Lys Lys
75                  80                  85

TAGGCTGCAT CTCTGAGACT GCAATCCGCC CGCTTTCCCG AATCACCATG ATACTAGATA     328

ATGATCTGTC TTGATTGCTT ACAGTTAGTT TACCTGTCTA TCAAGTTAGA AAAACACGG      388

GTAGAAGAAT TTGGATCCCG GTTGGCACAT TCAAGGTGCA AGATG GGC TCC AGA        442
                                                  Met Gly Ser Arg
                                                  1

TCT TCT ACC AGG ATC CCG GTA CCT CTA ATG CTG ATC ATC CGA ACC            487
Ser Ser Thr Arg Ile Pro Val Pro Leu Met Leu Ile Ile Arg Thr
```

|     |     |     |     |     |     |     |     |     |     |     |     |     |     |     |      |
| --- | --- | --- | --- | --- | --- | --- | --- | --- | --- | --- | --- | --- | --- | --- | ---- |
|  5  |     |     |     |     | 10  |     |     |     |     | 15  |     |     |     |     |      |
| GCG | CTG | ACA | CTG | AGC | TGT | ATC | CGT | CTG | ACA | AGC | TCT | CTT | GAT | GGC | 532  |
| Ala | Leu | Thr | Leu | Ser | Cys | Ile | Arg | Leu | Thr | Ser | Ser | Leu | Asp | Gly |      |
| 20  |     |     |     |     | 25  |     |     |     |     | 30  |     |     |     |     |      |
| AGG | CCT | CTT | GCG | GCT | GCA | GGG | ATC | GTG | GTA | ACA | GGA | GAT | AAA | GCA | 577  |
| Arg | Pro | Leu | Ala | Ala | Ala | Gly | Ile | Val | Val | Thr | Gly | Asp | Lys | Ala |      |
| 35  |     |     |     |     | 40  |     |     |     |     | 45  |     |     |     |     |      |
| GTC | AAC | ATA | TAC | ACC | TCA | TCC | CAG | ACA | GGG | TCA | ATC | ATA | GTT | AAG | 622  |
| Val | Asn | Ile | Tyr | Thr | Ser | Ser | Gln | Thr | Gly | Ser | Ile | Ile | Val | Lys |      |
| 50  |     |     |     |     | 55  |     |     |     |     | 60  |     |     |     |     |      |
| TTA | CTC | CCG | AAT | ATG | CCC | AAG | GAC | AAA | GAG | GTG | TGT | GCA | AAA | GCC | 667  |
| Leu | Leu | Pro | Asn | Met | Pro | Lys | Asp | Lys | Glu | Val | Cys | Ala | Lys | Ala |      |
| 65  |     |     |     |     | 70  |     |     |     |     | 75  |     |     |     |     |      |
| CCA | TTG | GAG | GCA | TAC | AAC | AGG | ACA | CTG | ACT | ACT | TTA | CTC | ACC | CCC | 712  |
| Pro | Leu | Glu | Ala | Tyr | Asn | Arg | Thr | Leu | Thr | Thr | Leu | Leu | Thr | Pro |      |
| 80  |     |     |     |     | 85  |     |     |     |     | 90  |     |     |     |     |      |
| CTT | GGT | GAT | TCT | ATC | CGC | AGG | ATA | CAA | GAG | TCT | GTG | ACT | ACT | TCC | 757  |
| Leu | Gly | Asp | Ser | Ile | Arg | Arg | Ile | Gln | Glu | Ser | Val | Thr | Thr | Ser |      |
| 95  |     |     |     |     | 100 |     |     |     |     | 105 |     |     |     |     |      |
| GGA | GGA | AGG | AGA | CAG | AGA | CGC | TTT | ATA | GGT | GCC | ATT | ATC | GGC | AGT | 802  |
| Gly | Gly | Arg | Arg | Gln | Arg | Arg | Phe | Ile | Gly | Ala | Ile | Ile | Gly | Ser |      |
| 110 |     |     |     |     | 115 |     |     |     |     | 120 |     |     |     |     |      |
| GTA | GCT | CTT | GGG | GTT | GCG | ACA | GCT | GCA | CAG | ATA | ACA | GCA | GCT | TCG | 847  |
| Val | Ala | Leu | Gly | Val | Ala | Thr | Ala | Ala | Gln | Ile | Thr | Ala | Ala | Ser |      |
| 125 |     |     |     |     | 130 |     |     |     |     | 135 |     |     |     |     |      |
| GCC | CTG | ATA | CAA | GCC | AAC | CAG | AAT | GCT | GCC | AAC | ATC | CTC | CGG | CTT | 892  |
| Ala | Leu | Ile | Gln | Ala | Asn | Gln | Asn | Ala | Ala | Asn | Ile | Leu | Arg | Leu |      |
| 140 |     |     |     |     | 145 |     |     |     |     | 150 |     |     |     |     |      |
| AAA | GAG | AGC | ATT | GCT | GCA | ACC | AAT | GAA | GCT | GTG | CAC | GAG | GTC | ACT | 937  |
| Lys | Glu | Ser | Ile | Ala | Ala | Thr | Asn | Glu | Ala | Val | His | Glu | Val | Thr |      |
| 155 |     |     |     |     | 160 |     |     |     |     | 175 |     |     |     |     |      |
| GAC | GGA | TTA | TCA | CAA | CTA | GCA | GTG | GCA | GTA | GGG | AAG | ATG | CAA | CAG | 982  |
| Asp | Gly | Leu | Ser | Gln | Leu | Ala | Val | Ala | Val | Gly | Lys | Met | Gln | Gln |      |
| 180 |     |     |     |     | 185 |     |     |     |     | 190 |     |     |     |     |      |
| TTT | GTC | AAT | GAC | CAG | TTC | AAT | AAT | ACA | GCG | CAA | GAA | TTG | GAC | TGT | 1027 |
| Phe | Val | Asn | Asp | Gln | Phe | Asn | Asn | Thr | Ala | Gln | Glu | Leu | Asp | Cys |      |
| 195 |     |     |     |     | 200 |     |     |     |     | 205 |     |     |     |     |      |
| ATA | AAA | ATT | GCA | CAG | CAG | GTC | GGT | GTA | GAA | CTC | AAC | TTG | TAC | CTA | 1072 |
| Ile | Lys | Ile | Ala | Gln | Gln | Val | Gly | Val | Glu | Leu | Asn | Leu | Tyr | Leu |      |
| 210 |     |     |     |     | 215 |     |     |     |     | 220 |     |     |     |     |      |
| ACT | GAA | TTG | ACT | ACA | GTA | TTT | GGG | CCA | CAA | ATC | ACT | TCC | CCT | GCC | 1117 |
| Thr | Glu | Leu | Thr | Thr | Val | Phe | Gly | Pro | Gln | Ile | Thr | Ser | Pro | Ala |      |
| 225 |     |     |     |     | 230 |     |     |     |     | 235 |     |     |     |     |      |
| TTA | ACT | CAG | CTG | ACT | ATC | CAA | GCG | CTT | TAC | AAT | CTA | GCT | GGT | GGT | 1162 |
| Leu | Thr | Gln | Leu | Thr | Ile | Gln | Ala | Leu | Tyr | Asn | Leu | Ala | Gly | Gly |      |
| 240 |     |     |     |     | 245 |     |     |     |     | 250 |     |     |     |     |      |
| AAT | ATG | GAT | TAC | TTG | CTG | ACT | AAG | TTA | GGT | GTA | GGG | AAC | AAC | CAA | 1207 |
| Asn | Met | Asp | Tyr | Leu | Leu | Thr | Lys | Leu | Gly | Val | Gly | Asn | Asn | Gln |      |
| 255 |     |     |     |     | 260 |     |     |     |     | 265 |     |     |     |     |      |
| CTC | AGC | TCA | TTA | ATT | GGT | AGC | GGC | TTG | ATC | ACC | GGC | AAC | CCT | ATT | 1252 |
| Leu | Ser | Ser | Leu | Ile | Gly | Ser | Gly | Leu | Ile | Thr | Gly | Asn | Pro | Ile |      |
| 270 |     |     |     |     | 275 |     |     |     |     | 280 |     |     |     |     |      |
| CTG | TAC | GAC | TCA | CAG | ACT | CAG | ATC | TTG | GGT | ATA | CAG | GTA | ACT | TTG | 1297 |
| Leu | Tyr | Asp | Ser | Gln | Thr | Gln | Ile | Leu | Gly | Ile | Gln | Val | Thr | Leu |      |
| 285 |     |     |     |     | 290 |     |     |     |     | 295 |     |     |     |     |      |
| CCT | TCA | GTT | GGG | AAC | CTG | AAT | AAT | ATG | CGT | GCC | ACC | TAC | CTG | GAG | 1342 |
| Pro | Ser | Val | Gly | Asn | Leu | Asn | Asn | Met | Arg | Ala | Thr | Tyr | Leu | Glu |      |
| 300 |     |     |     |     | 305 |     |     |     |     | 310 |     |     |     |     |      |
| ACC | TTA | TCT | GTA | AGC | ACA | ACC | AAG | GGA | TTT | GCC | TCA | GCA | CTT | GTC | 1387 |
| Thr | Leu | Ser | Val | Ser | Thr | Thr | Lys | Gly | Phe | Ala | Ser | Ala | Leu | Val |      |
| 315 |     |     |     |     | 320 |     |     |     |     | 325 |     |     |     |     |      |

| | | | | | | | | | | | | | | | |
|---|---|---|---|---|---|---|---|---|---|---|---|---|---|---|---|
| CCA | AAA | GTG | GTG | ACA | CAG | GTC | GGT | TCC | GTG | ATA | GAA | GAA | CTT | GAC | 1432 |
| Pro | Lys | Val | Val | Thr | Gln | Val | Gly | Ser | Val | Ile | Glu | Glu | Leu | Asp | |
| 330 | | | | | 335 | | | | | 340 | | | | | |

| | | | | | | | | | | | | | | | |
|---|---|---|---|---|---|---|---|---|---|---|---|---|---|---|---|
| ACC | TCA | TAC | TGT | ATA | GGG | ACC | GAC | TTG | GAT | TTA | TAC | TGT | ACA | AGA | 1477 |
| Thr | Ser | Tyr | Cys | Ile | Gly | Thr | Asp | Leu | Asp | Leu | Tyr | Cys | Thr | Arg | |
| 345 | | | | | 350 | | | | | 355 | | | | | |

| | | | | | | | | | | | | | | | |
|---|---|---|---|---|---|---|---|---|---|---|---|---|---|---|---|
| ATA | GTG | ACA | TTC | CCT | ATG | TCT | CCT | GGT | ATT | TAT | TCT | TGT | CTG | AGC | 1522 |
| Ile | Val | Thr | Phe | Pro | Met | Ser | Pro | Gly | Ile | Tyr | Ser | Cys | Leu | Ser | |
| 360 | | | | | 365 | | | | | 370 | | | | | |

| | | | | | | | | | | | | | | | |
|---|---|---|---|---|---|---|---|---|---|---|---|---|---|---|---|
| GGT | AAT | ACA | TCG | GCT | TGC | ATG | TAT | TCA | AAG | ACT | GAA | GGC | GCA | CTT | 1567 |
| Gly | Asn | Thr | Ser | Ala | Cys | Met | Tyr | Ser | Lys | Thr | Glu | Gly | Ala | Leu | |
| 375 | | | | | 380 | | | | | 385 | | | | | |

| | | | | | | | | | | | | | | | |
|---|---|---|---|---|---|---|---|---|---|---|---|---|---|---|---|
| ACT | ACG | CCA | TAT | ATG | GCT | CTC | AAA | GGC | TCA | GTT | ATT | GCC | AAT | TGC | 1612 |
| Thr | Thr | Pro | Tyr | Met | Ala | Leu | Lys | Gly | Ser | Val | Ile | Ala | Asn | Cys | |
| 390 | | | | | 395 | | | | | 400 | | | | | |

| | | | | | | | | | | | | | | | |
|---|---|---|---|---|---|---|---|---|---|---|---|---|---|---|---|
| AAG | CTG | ACA | ACA | TGT | AGA | TGT | GCA | GAT | CCC | CCA | GGT | ATC | ATA | TCG | 1657 |
| Lys | Leu | Thr | Thr | Cys | Arg | Cys | Ala | Asp | Pro | Pro | Gly | Ile | Ile | Ser | |
| 405 | | | | | 410 | | | | | 415 | | | | | |

| | | | | | | | | | | | | | | | |
|---|---|---|---|---|---|---|---|---|---|---|---|---|---|---|---|
| CAA | AAT | TAT | GGA | GAA | GCT | GTG | TCC | TTA | ATA | GAT | AGG | CAC | TCA | TGC | 1702 |
| Gln | Asn | Tyr | Gly | Glu | Ala | Val | Ser | Leu | Ile | Asp | Arg | His | Ser | Cys | |
| 420 | | | | | 425 | | | | | 430 | | | | | |

| | | | | | | | | | | | | | | | |
|---|---|---|---|---|---|---|---|---|---|---|---|---|---|---|---|
| AAC | GTC | TTA | TCC | TTA | GAC | GGG | ATA | ACT | CTG | AGG | CTC | AGT | GGG | GAA | 1747 |
| Asn | Val | Leu | Ser | Leu | Asp | Gly | Ile | Thr | Leu | Arg | Leu | Ser | Gly | Glu | |
| 435 | | | | | 440 | | | | | 445 | | | | | |

| | | | | | | | | | | | | | | | |
|---|---|---|---|---|---|---|---|---|---|---|---|---|---|---|---|
| TTT | GAT | GCA | ACC | TAT | CAA | AAG | AAT | ATC | TCT | ATA | CTA | GAT | TCT | CAA | 1792 |
| Phe | Asp | Ala | Thr | Tyr | Gln | Lys | Asn | Ile | Ser | Ile | Leu | Asp | Ser | Gln | |
| 450 | | | | | 455 | | | | | 460 | | | | | |

| | | | | | | | | | | | | | | | |
|---|---|---|---|---|---|---|---|---|---|---|---|---|---|---|---|
| GTT | ATA | GTG | ACA | GGC | AAT | CTT | GAT | ATA | TCA | ACT | GAG | CTT | GGG | AAT | 1837 |
| Val | Ile | Val | Thr | Gly | Asn | Leu | Asp | Ile | Ser | Thr | Glu | Leu | Gly | Asn | |
| 465 | | | | | 470 | | | | | 475 | | | | | |

| | | | | | | | | | | | | | | | |
|---|---|---|---|---|---|---|---|---|---|---|---|---|---|---|---|
| GTC | AAC | AAC | TCA | ATA | AGT | AAT | GCC | CTG | AAT | AAG | TTA | GAG | GAA | AGC | 1882 |
| Val | Asn | Asn | Ser | Ile | Ser | Asn | Ala | Leu | Asn | Lys | Leu | Glu | Glu | Ser | |
| 480 | | | | | 485 | | | | | 490 | | | | | |

| | | | | | | | | | | | | | | | |
|---|---|---|---|---|---|---|---|---|---|---|---|---|---|---|---|
| AAC | AGC | AAA | CTA | GAC | AAA | GTC | AAT | GTC | AAA | CTG | ACC | AGC | ACA | TCT | 1927 |
| Asn | Ser | Lys | Leu | Asp | Lys | Val | Asn | Val | Lys | Leu | Thr | Ser | Thr | Ser | |
| 495 | | | | | 500 | | | | | 505 | | | | | |

| | | | | | | | | | | | | | | | |
|---|---|---|---|---|---|---|---|---|---|---|---|---|---|---|---|
| GCT | CTC | ATT | ACC | TAC | ATC | GTT | TTA | ACT | GTC | ATA | TCT | CTT | GTT | TTT | 1972 |
| Ala | Leu | Ile | Thr | Tyr | Ile | Val | Leu | Thr | Val | Ile | Ser | Leu | Val | Phe | |
| 510 | | | | | 515 | | | | | 520 | | | | | |

| | | | | | | | | | | | | | | | |
|---|---|---|---|---|---|---|---|---|---|---|---|---|---|---|---|
| GGT | GTA | CTT | AGC | CTG | GTT | CTA | GCA | TGC | TAC | CTG | ATG | TAC | AAG | CAA | 2017 |
| Gly | Val | Leu | Ser | Leu | Val | Leu | Ala | Cys | Tyr | Leu | Met | Tyr | Lys | Gln | |
| 525 | | | | | 530 | | | | | 535 | | | | | |

| | | | | | | | | | | | | | | | |
|---|---|---|---|---|---|---|---|---|---|---|---|---|---|---|---|
| AAG | GCA | CAA | CAA | AAG | ACC | TTG | TTA | TGG | CTT | GGG | AAT | AAT | ACC | CTT | 2062 |
| Lys | Ala | Gln | Gln | Lys | Thr | Leu | Leu | Trp | Leu | Gly | Asn | Asn | Thr | Leu | |
| 540 | | | | | 545 | | | | | 550 | | | | | |

| | | | | | | | | | | | |
|---|---|---|---|---|---|---|---|---|---|---|---|
| GAT | CAG | ATG | AGA | GCC | ACT | ACA | AAA | ATA | TGAATACA | AACGAGAGGC | GGAGG | 2112 |
| Asp | Gln | Met | Arg | Ala | Thr | Thr | Lys | Ile | | | |
| 555 | | | | | 560 | | | | | | |

TATCC CCAATAGCAA TTTGCGTGTA AATTCTGGCA ACCTGTTAAT TAGAAGAATT AAGAA 2172
AAAA 2176

( 2 ) INFORMATION FOR SEQ ID NO:3:

( i ) SEQUENCE CHARACTERISTICS:
        ( A ) LENGTH:21 base pairs
        ( B ) TYPE:nucleic acid
        ( C ) STRANDEDNESS:single
        ( D ) TOPOLOGY:linear ( i i ) MOLECULE TYPE:synthetic oligonucleotide
        ( A ) DESCRIPTION:sequence of synthetic oligonucleotide used for
           the mutagenesis of the RR2 gene (sequence 5'to 3')

( i v ) ANTI-SENSE:yes ( x i ) SEQUENCE DESCRIPTION:SEQ ID NO:3:

GCAGCATGCC CGGGGTTGTT C                       21

( 2 ) INFORMATION FOR SEQ ID NO:4:

( i ) SEQUENCE CHARACTERISTICS:
        ( A ) LENGTH:21 base pairs
        ( B ) TYPE:nucleic acid
        ( C ) STRANDEDNESS:single
        ( D ) TOPOLOGY:linear ( i i ) MOLECULE TYPE:synthetic oligonucleotide
        ( A ) DESCRIPTION:sequence of synthetic oligonucleotide used for
            the mutagenesis of the RR2 gene (sequence 5'to 3')

( i v ) ANTI-SENSE:no ( x i ) SEQUENCE DESCRIPTION:SEQ ID NO:4:

CCGATTCACG TCGACTTTAG G                       21

( 2 ) INFORMATION FOR SEQ ID NO:5:

( i ) SEQUENCE CHARACTERISTICS:
        ( A ) LENGTH:21 base pairs
        ( B ) TYPE:nucleic acid
        ( C ) STRANDEDNESS:single
        ( D ) TOPOLOGY:linear ( i i ) MOLECULE TYPE:synthetic oligonucleotide
        ( A ) DESCRIPTION:sequence of synthetic oligonucleotide used for
            the mutagenesis of the RR2 gene (sequence 5'to 3')

( i v ) ANTI-SENSE:yes ( x i ) SEQUENCE DESCRIPTION:SEQ ID NO:5:

GGGTTGTCCA TGGCGGCTAT A                       21

( 2 ) INFORMATION FOR SEQ ID NO:6:

( i ) SEQUENCE CHARACTERISTICS:
        ( A ) LENGTH:22 base pairs
        ( B ) TYPE:nucleic acid
        ( C ) STRANDEDNESS:single
        ( D ) TOPOLOGY:linear ( i i ) MOLECULE TYPE:synthetic oligonucleotide
        ( A ) DESCRIPTION:sequence of synthetic oligonucleotide used for
            the mutagenesis of the fusion protein gene
            ( s e q u e n c e  5   t o  3  )

( i v ) ANTI-SENSE:no ( x i ) SEQUENCE DESCRIPTION:SEQ ID NO:6:

CAAGGTGCAC CATGGGCTCC AG                       22

( 2 ) INFORMATION FOR SEQ ID NO:7:

( i ) SEQUENCE CHARACTERISTICS:
        ( A ) LENGTH:25 base pairs
        ( B ) TYPE:nucleic acid
        ( C ) STRANDEDNESS:single
        ( D ) TOPOLOGY:linear ( i i ) MOLECULE TYPE:synthetic oligonucleotide
        ( A ) DESCRIPTION:sequence of synthetic oligonucleotide used for
            the mutagenesis of the fusion protein gene
            ( s e q u e n c e  5   t o  3  )

( i v ) ANTI-SENSE:yes ( x i ) SEQUENCE DESCRIPTION:SEQ ID NO:7:

GCTATTGGGG ATATCTCCGC CTCTC                   25

RECOMBINANT HERPESVIRUSES, IN PARTICULAR FOR THE PRODUCTION OF VACCINES, PROCESS FOR PREPARING THEM, PLASMIDS PRODUCED DURING THIS PROCESS AND VACCINES OBTAINED

The present invention relates to recombinant herpesviruses capable of being used, in particular, in vaccines against virus diseases of man and animals, to a process for preparing them, to the plasmids produced during this process and also to the vaccines obtained. It also relates to a nucleotide sequence corresponding to a portion of the genome of the turkey herpesvirus (HVT), which sequence is capable of being used for the preparation of such viruses.

The turkey herpesvirus (HVT) of the subfamily gammaherpesvirinae is a naturally non-pathogenic and non-oncogenic virus serologically related to the oncogenic virus of Marek's disease, the agent responsible for a lymphoproliferative disease of poultry of considerable economic importance.

These two viruses possess numerous sequence homologies over the whole length of their genome, and recent published data show, in addition, a similarity with the genomes of the herpes simplexviruses(HSV) or the varicella virus (VZV), which suggests at the present time their classification in the family of the alphaherpesviruses rather than that of the gammaherpesviruses, where they were classified on grounds of their tropism (1) (for the bibliographic references, see Appendix 1).

For many years, vaccination using the HVT virus has been very effective for controlling Marek's disease. Nevertheless, the emergence of new highly virulent strains shows the need to use vaccines closer antigenically to the wild-type virus. In this context, vaccines obtained by genetic manipulation are an important possibility.

Live viral vectors such as attenuated strains of poxviruses or of herpesviruses are being developed increasingly. Thus, the HSV virus or Aujeszky's disease virus (PRV) have been used as vectors for the expression of foreign genes (26, 34). For this purpose, the foreign genes were inserted into cloned fragments of non-essential regions of the herpes genomes and then introduced into the viral vector by homologous recombination. This last step is performed simply by cotransfection, since the DNAs of herpesviruses are naturally infectious.

The HVT virus is a candidate of choice for the development of such a viral vector in the avian field, since it has the twofold advantage of being able to be used for its vaccinal properties and as a vaccine for other diseases. In addition, this virus gives rise to a permanent viraemia and may be used in embryo vaccination.

It is possible to insert within the HVT genome genes coding for immunogens of Marek's disease virus, thereby boosting the protective role of the HVT virus. It is also possible to insert within the HVT genome genes coding for immunogens of viral, bacterial or parasitic pathogenic agents of other avian diseases such as Marek's disease (MDV), infectious bronchitis (IBV), Newcastle disease (NDV), fowl plague, Gumboro disease (IBDV), avian anaemia (CAA), egg drop syndrome, coccidiosis, fowlpox, infectious rhinotracheitis, colibacillosis, pasteurellosis and haemophilosis. The HVT virus thus appears to offer itself as a versatile chimera.

The genetic material of herpesviruses consists of a double-stranded DNA containing 100,000 to 180,000 base pairs. Different regions of this genome have been shown to be non-essential to viral replication, and are hence potential sites for insertion of foreign genes or of deletion for the creation of new, more attenuated strains.

Some of these regions are associated with virulence, and their modification causes a decrease in the pathogenicity of the viruses. Thus, the inactivation of thymidine kinase renders human herpes simplex non-pathogenic and does not prevent viral growth in vitro (3, 8, 21, 33); the same applies to the PRV virus (30). In addition, it has been shown that attenuation of the Bartha strain of the PRV virus is linked to a deletion of the glycoprotein gI, the gene for which occurs in the small fragment Us (18).

Other herpesvirus genes have been identified as non-essential to viral growth without, however, being associated with phenomena of virulence. Among these genes, the UL24 gene of the HSV virus (23), various genes of the HSV virus located in the small fragment Us (35), the gene for the glycoprotein gIII of the virus (BHV) of infectious bovine rhinotracheitis (9) and the gene for the glycoprotein gX of the PRV virus (34) may be mentioned.

Ribonucleotide reductase is an important enzyme of the chain of DNA biosynthesis, responsible for the reduction of ribonucleotides to deoxyribonucleotides. Herpesviruses possess a ribonucleotide reductase activity of their own, corresponding to criteria of regulation different from those of the cellular enzyme (12, 13). Like the bacterial or mammalian enzyme, ribonucleotide reductase of herpesviruses consists of 2 heterologous subunits whose interaction is necessary to the enzymatic activity: large subunit RR1 and small subunit RR2.

The genes coding for these proteins have been localised and sequenced for the herpes simplex virus (HSV), the varicella virus (VZV) and the Epstein-Barr virus (EBV), and their mode of transcription studied in the case of the HSV virus (15, 16, 27, 28). Recently, Goldstein and Weller (1988), by inserting the lacZ gene of the beta-galactosidase in frame in the terminal region of the gene coding for the large subunit of ribonucleotide reductase of the HSV virus, have shown the non-essential character of this gene. Mutants deleted in this same gene of the HSV virus were constructed, and their study demonstrates that ribonucleotide reductase is not necessary to viral multiplication in cells in an exponential growth phase, the enzyme of cellular origin then being capable of compensating for this deletion (4, 5).

Nevertheless, even when they are cultured on cells possessing trans-complementing ribonucleotide reductase activity, the deleted mutants undergo a modification of their growth (5). This phenomenon is considerably magnified when these mutants are cultured at 39.5° C. or on cells deprived of serum (20). Still more recently, it has been shown that deletion of the large subunit of ribonucleotide reductase brings about a decrease in the virulence of the HSV virus in mice (7).

There are, to date, no published data relating to the essential role of ribonucleotide reductase of the HVT virus. There is no sequence relating to the small subunit RR2 of the ribonucleotide reductase gene of the HVT virus.

The objective of the present invention is hence to provide recombinant viruses or chimeric viruses capable of multiplying normally, in particular for the production of effective vaccines.

The cloning and sequencing of the portion of the turkey herpesvirus (HVT) genome which corresponds to the gene for the small subunit RR2 of ribonucleotide reductase were first carried out.

Surprisingly, the gene coding for the small subunit RR2 could be mutated or completely deleted and replaced by a coding sequence without the mutant thus created exhibiting an impairment as regards its growth. It was thus demonstrated that the HVT virus can be used effectively as an expression vector by inserting a foreign gene into the gene for the small subunit RR2, this being effected, in particular, under the control of the promoter or promoters of the small subunit RR2 of ribonucleotide reductase.

The invention is also directed towards the use of different naturally non-pathogenic and non-oncogenic herpesviruses, or, where appropriate, herpesviruses rendered non-pathogenic and non-oncogenic, as live viral vectors for the production of recombinant viruses having satisfactory growth rates, and, where appropriate, of recombinant vaccines.

The subject of the invention is hence the nucleotide sequence, and its variants, which corresponds to the gene for the small subunit RR2 of ribonucleotide reductase of the HVT virus.

This sequence may be combined with other common fragments such as promoters, initiation or stop signals or introns or other non-coding sequences at the 3' and/or 5' end. It also includes the variants obtained, in particular, by substitution of codons or of nucleotides preserving the meaning of the code, or by substitutions, insertions or deletions coding for an equivalent polypeptide and, in particular, preserving the antigenicity of the polypeptide. It also includes any fragment enabling a polypeptide preserving this antigenicity to be expressed.

The invention also relates to the different restriction or synthetic fragments originating from the sequence according to the invention, and in particular any fragment capable of hybridising with the gene for the small subunit RR2 of HVT or any other herpesvirus.

The subject of the invention is also a recombinant HVT virus comprising a heterologous gene inserted into the region of the genome of the virus corresponding to the gene for the small subunit RR2 of ribonucleotide reductase, so as to be capable of being expressed. Heterologous gene is understood, in particular, to mean a gene coding for an immunogenic protein or glycoprotein of a viral, bacterial or parasitic pathogenic agent. In the case of a viral vector consisting of the HVT virus, the heterologous gene may be, in particular, a gene coding for an immunogen of the virus of Marek's disease, of infectious avian bronchitis, of Newcastle disease, of fowl plague, of Gumboro disease, of avian anaemia, of egg drop syndrome, of the agent of coccidiosis, of fowlpox, of infectious laryngotracheitis, of colibacillosis, of pasteurellosis or of haemophilosis.

Heterologous gene is also understood to mean any other gene foreign to the HVT virus and coding for a peptide or protein, for example hormones, growth factors, and the like.

The invention also applies to a recombinant virus chosen from the virus of Aujeszky's disease (PRV), of infectious bovine rhinotracheitis (BHV), of infectious feline rhinotracheitis (FHV), of equine rhinopneumonia (EHV), of canine herpes (CHV) and of duck herpes, comprising a heterologous gene inserted into the region of the genome of the virus in question corresponding to the gene of the small subunit RR2 of ribonucleotide reductase.

The invention further applies to the recombinant human herpes simplex virus (HSV), varicella virus (VZV), cytomegalovirus (CMV) and Epstein-Barr virus (EBV) comprising a heterologous gene inserted in the same manner as above.

The inserted heterologous gene is preferably expressed under the control of the transcription regulation sequences of the gene for the small subunit RR2. It is, however, possible to contrive that this expression is under the control of promoter sequences, originating from the virus in question or from other herpesviruses, transferred to the genome of the said virus in question. The gene is placed downstream of the initiation signals in the correct reading frame for its expression.

Preferably, the initiation and termination codons of the RR2 gene are replaced by those of the gene to be inserted.

A further subject of the invention is a process for preparing a recombinant HVT virus, in which the heterologous gene is inserted into the region of the HVT genome which corresponds to the gene for the small subunit RR2 of ribonucleotide reductase.

The subject of the invention is also a process for preparing a recombinant virus from a virus chosen from other herpesviruses, in particular PRV, BHV, FHV, EHV, CHV and HSV, in which the heterologous gene is inserted into the region of the genome of the said virus which corresponds to the gene for the small subunit RR2 of ribonucleotide reductase.

The gene coding for the small subunit of ribonucleotide reductase of one of these viruses may be advantageously localised using a labelled DNA or RNA probe comprising all or part of the HVT RR2 gene, and hybridising the probe with the genomic RNA of the candidate herpesvirus digested after separation by the Western blotting technique using weakly stringent conditions. The fragments thus recognised may be cloned and sequenced in order to carry out the construction of the recombinant virus.

Preferably, the portion of the viral genome containing the gene for the small subunit RR2 is isolated, a partial or total deletion of this gene is preferably carried out and the heterologous gene is inserted into the region corresponding to the said gene before introducing the DNA fragment thereby obtained into the genome of the virus by cotransfection and homologous recombination.

Preferably, the transcription initiation and termination signals of the gene for the small subunit RR2 are retained. This expression may also be carried out under the control of promoter sequences originating from the virus in question, for example the promoter of the RR1 gene, of the TK gene, of the gA gene or of the gB gene, or of other herpesviruses, for example the promoter of the gI gene of the BHV virus or of the gII gene of the PRV virus, transferred to the genome of the virus in question.

In an embodiment applied to the HVT virus, a process for the construction of a recombinant virus can comprise the following steps:

a) a K1 Bam HI fragment of the HVT genome is isolated by digestion of the genome with the restriction enzyme Bam HI, b) this fragment is digested with the restriction enzyme Hind III, to obtain a fragment corresponding to the 5' portion of the RR2 gene and to the region upstream including the promoter, and a fragment corresponding to the 3' portion of the RR2 gene and to the region downstream of this gene, c) the two fragments thereby obtained in b) are cloned, respectively, into the vectors pUC 18 and pUC 19, d) these plasmids are digested, respectively, by the restriction enzyme systems Hind III/Aat II and Xmn I/Aat II to generate a new plasmid containing a deletion between the Hind III and Xmn I sites, e) restriction sites are created by directed mutagenesis in the plasmid obtained in d), permitting the correct insertion of the gene to be expressed, f) a heterologous gene, in particular a gene coding for an immunogen associated with an avian disease, is cloned into these restriction sites, and g) the DNA fragment obtained in f) is inserted into the genome of the HVT virus by cotransfection and homologous recombination.

A further subject of the invention is a recombinant virus obtained by the process according to the invention.

A further subject of the invention is a plasmid containing a portion of the genome of the HVT virus which contains the gene for the small subunit RR2.

The subject of the invention is also a plasmid containing a portion of the genome of a herpesvirus, preferably chosen from PRV, BHV, EHV, FHV, CHV and HSV, which contains the gene for the small subunit RR2 of ribonucleotide reductase of the said virus.

Preferably, the portion of the genome contained in the plasmid comprises a deletion in the region corresponding to the gene for the small subunit RR2. As a further preference, a heterologous gene, for example a gene coding for an immunogen, is inserted into the said region corresponding to the gene for the small subunit RR2.

In the case of the HVT virus, a further subject of the invention is a plasmid containing the K1 Bam HI fragment of the HVT virus containing the gene for the small subunit RR2 of ribonucleotide reductase. Preferably, this fragment comprises a deletion of 766 bases between the initial Hind III and Xmn I sites. As a further preference, a heterologous gene coding for an immunogen of an avian disease is inserted into the region of this fragment which corresponds to the gene for the small subunit RR2 of ribonucleotide reductase.

A further subject of the invention is recombinant HVT viruses comprising the recombined genome fragment of the plasmid produced from the genome of the said virus.

The invention also relates to recombinant PRV, BHV, EHV, FHV, CHV and HSV viruses comprising the recombined genome fragment of the plasmid produced from the genome of the virus in question.

A further subject of the invention is a vaccine comprising a recombinant virus obtained as above. The excipients and diluents will be, in particular, those customarily used for the preparation of such vaccines, in particular the live vaccines in question.

The invention will now be described in greater detail. A description will be given first of the cloning and sequencing of the gene for the small subunit RR2 of ribonucleotide reductase of the HVT virus, and then of the introduction of a deletion in the gene for the small subunit of HVT and the demonstration of the non-essential character of this small subunit in the viral multiplication. The insertion of heterologous genes into the viral vector and their expression will then be dealt with.

The detailed description will be given with reference to the attached drawing, wherein.

MATERIALS AND METHODS

Figure 1:
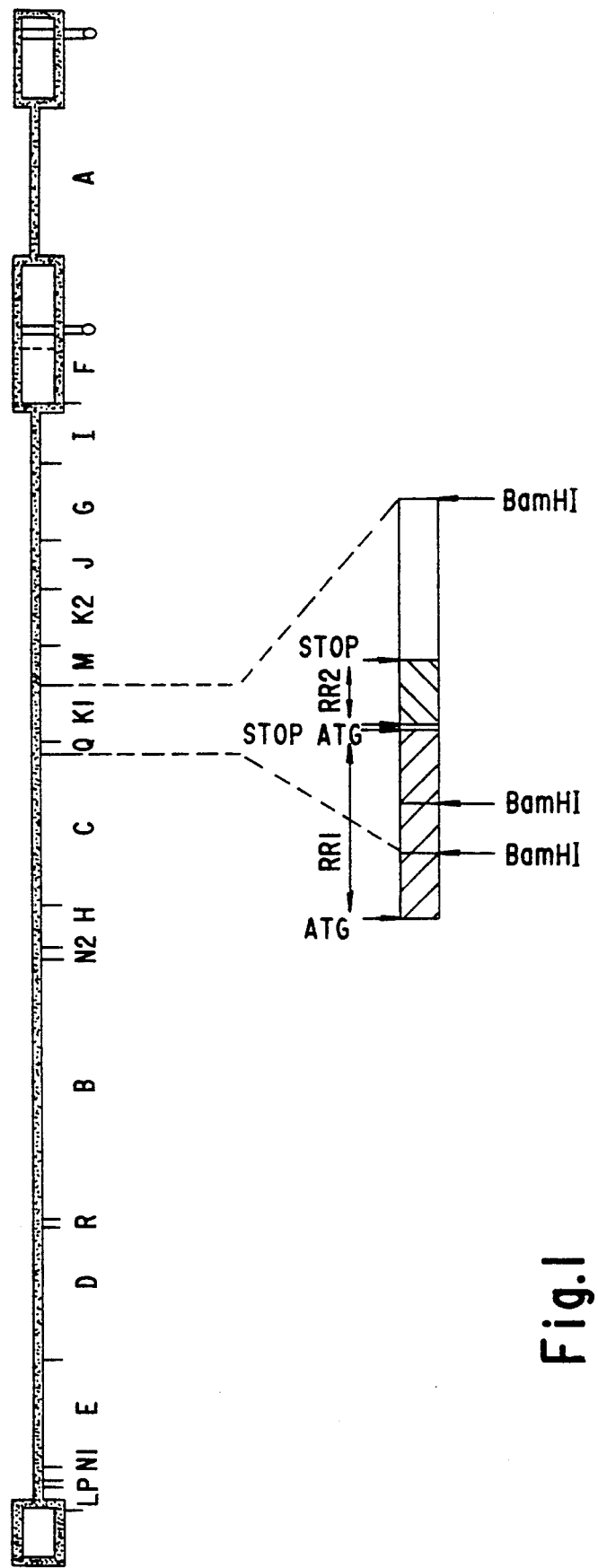
FIG. 1 shows the restriction map of the genome of the HVT virus and the localisation of the RR2 gene.

Generally speaking, the techniques used for the construction of recombinant plasmids are those described by T. Maniatis et al. (17). For all the steps of cloning or subcloning, the vector linearised with the appropriate restriction enzymes is dephosphorylated before ligation.

Purification of the DNA fragments from an agarose gel is carried out according to the technique described by the manufacturer: "Geneclean" (Bio 101, San Diego, Calif., USA).

Viral strain

HVT virus strain FC 126 was isolated in 1968 by Dr. Witter of the Regional Poultry Research Laboratory (USDA, East Lansing, Mich., USA), in a flock of turkeys aged 23 weeks (36).

It was then passaged 10 times through duck fibroblasts and thereafter underwent 9 further passages through SPF chick embryo fibroblasts.

The viral DNA used for this work was extracted from viruses which had been subjected to a total of 23 to 24 passages from the original isolate.

Cell culture

Chick embryo fibroblasts are cultured in F10-199 medium (Rhône-Mérieux, Lyon, France) supplemented with foetal calf serum.

Cells intended for production of the virus used for purifying the DNA were cultured in roller bottles.

For the transfection experiments, cells were cultured in 10-cm Petri dishes or on 24-well dishes.

Isolation of HVT virus DNA for cloning

Confluent monolayers of chick fibroblasts are infected with HVT virus and left incubating for 1 to 3 days at 39° C.±1° C. When the cytopathic effect due to the virus is considered optimal, the infected cells are detached from the walls of the roller bottles and then centrifuged. The pellets of infected cells are resuspended in a stabiliser containing sucrose and bovine albumin. The cell suspension thus prepared is immersed in a bath of ice-cold water and then treated with ultrasound. The suspension is then clarified by low speed centrifugation and centrifuged for 1 h at 40,000 rpm with a Ti 45 rotor (Beckman, Palo Alto, Calif., USA).

The viral pellet, taken up in buffer (10 mM tris; 136 mM NaCl; 2.6 mM KCl; 20 mM $MgCl_2$; 1.8 mM $CaCl_2$), is purified by centrifugation on a sucrose zonal gradient (30%, 50%, w/v) for 20 h at 23,000 rpm with an SW28 rotor (Beckman). The virus obtained in the fraction corresponding to a sucrose density corresponding to a concentration of approximately 48% is recovered. After dilution in 50 mM tris buffer/10 mM EDTA, the virus is sedimented by centrifugation for 40 min. at 40,000 rpm with an SW41 rotor (Beckman). The viral DNA is then extracted by treating the purified virus with proteinase K at a concentration of 100 µg/ml for 2 h at 37° C. in the presence of 0.5% SDS, and thereafter purified by a phenol treatment followed by 3 treatments with chloroform/isoamyl alcohol (24:1). The viral DNA is then precipitated with ethanol at −20° C.

Isolation of infectious DNA for the transfection experiments.

HVT virus associated with the cells is inoculated into confluent monolayers of chick fibroblasts at a multiplicity of infection of approximately 0.001 pfu (plaque forming unit) per cell.

The infected cells are incubated at 37° C. in F10-199 medium supplemented with 2% of foetal calf serum.

When the cytopathic effect is maximal (2 to 3 days), the medium is removed and the infected cells are harvested after trypsinisation and then sedimented by low speed centrifugation.

The pellet containing the infected cells is taken up in 10 mM tris buffer/1 mM EDTA, pH 8, containing 0.5% (w/v) of Triton X-100 and 0.5% (w/v) of NP40, on the basis of $2 \times 10^8$ infected cells per ml of buffer, the cells being treated as described by Lee et al., 1980 (14).

The virus is then obtained by centrifugation on a 15%–30% (w/v) sucrose gradient for 24 min. at 22,000 rpm as described by Lee et al.

The viral DNA is extracted from the purified viruses by treatment with proteinase K (400 µg/ml final) and 0.5% (w/v) SDS overnight at 37° C., and then purified by zonal centrifugation on a 10%–30% (v/v) glycerol gradient for 4 h 30 min. at 38,000 rpm with an SW41 rotor.

The viral DNA is then precipitated with alcohol and taken up in 10 mM tris buffer/1 mM EDTA, pH 7.5.

DNA cloning

The viral DNA was digested with the restriction enzyme Bam HI and the fragments were cloned into plasmid pUC 18 (38) digested beforehand with Bam HI and dephosphorylated.

*E. coli* bacteria NM 522 (6) were transformed according to the calcium chloride procedure and then cultured in the presence of ampicillin and Xgal.

The colourless colonies were cultured in small volumes and the plasmid DNA was extracted.

Clones were selected on the basis of the size of the inserts, determined by electrophoresis on 0.8% agarose gel after Bam HI digestion.

Sequencing

The nucleotide sequences were determined according to the dideoxynucleotide technique described by Sanger, 1977 (24), using the Sequanase version 2 kit (USB, Cleveland, Ohio, USA) according to the protocol described by the manufacturer (29), employing specific synthetic oligonucleotides (Applied Biosystems, Forster City, Calif., USA).

Directed mutagenesis

DNA fragments cloned into phage M13 were mutagenised according to the technique described by the manufacturer of the in vitro mutagenesis kit (Amersham, Buckinghamshire, Great Britain) (19, 31, 32).

DNA fragments cloned into the vector Blue Script SK+ (Stratagene, La Jolla, Calif., USA) were mutagenised after separation of single-stranded DNA's using R408 helper phage (Stratagene, La Jolla, Calif., USA) (22). The procedure for mutagenesis and selection of the mutants using *E. coli* strain CJ236 dut⁻ ung⁻ (In Vitrogen, San Diego, Calif., USA) has been described by T. Kunkel et al. (10, 11).

Transfection

Primary chick embryo cells, cultured to confluence (24 h), were cotransfected with HVT viral DNA and the DNA of a plasmid containing the gene to be inserted, flanked at the 5' and 3' ends by regions of the HVT genome so as to permit homologous recombination.

The technique used is the Lipofectine ® technique described by the manufacturer (BRL, Bethesda Research Laboratory, Gaithersburg, Madison, USA) (2).

1 µg of viral DNA was mixed with 1 to 10 µg of DNA of the linearised plasmid in a volume of 50 µl, and then added to 50 µl of Lipofectine reagent.

The mixture was left for 30 min. at room temperature and then added to the cells which had been rinsed beforehand with serum-free medium. The adsorption was carried out for 5 h at 37° C. under a $CO_2$ atmosphere in the presence of 3 ml of serum-free medium (BRL optimum). After 5 h, foetal calf serum was added to a final concentration of 8% and culturing was continued for 72 h or longer.

The first indications of a cytopathogenic effect appeared after 72 h.

The cells were sometimes trypsinised after 72 h, then reinoculated (1:1 or 1:2) in a secondary passage, in F10-199 medium, and incubated at 37° C. until lytic plaques appeared (not less than 72 h), this being done in order to increase the cytopathogenic effect.

On average, 200 plaques per µg of HVT DNA were obtained.

After the appearance of viral foci, the medium is removed and then replaced by F10-199 medium supplemented with 2% of foetal calf serum and containing 1% of agarose.

The infected cells were recovered by punching out samples and extracting the latter, dissociated by adding a drop of trypsin solution (0.04% and inoculated into a cell culture.

EXAMPLE 1

CLONING OF THE RIBONUCLEOTIDE REDUCTASE GENE AND DETERMINATION OF IT NUCLEOTIDE SEQUENCE

It was shown by Buckmaster et al. that the gene for the large subunit of ribonucleotide reductase of the HVT virus could be localised either in the K1 Bam HI restriction fragment or in the K2 Bam HI fragment (1).

pUC 18 plasmids containing an insert corresponding in size to that of the K1/K2 fragment (namely 4.2 kilobases), which are described above (DNA cloning), were hence selected and the ends of the inserts then sequenced. The sequences obtained were compared, using a Microgenie sequence analysis programme (Beckman), with the published sequences of ribonucleotide reductase of VZV, HSV and EBV viruses. The sequence homology enabled plasmid pHVT K1 to be adopted. This plasmid contains the whole of the gene for the small subunit RR2 of ribonucleotide reductase and the 3' region of the gene for the large subunit RR1.

The sequence of the ribonucleotide reductase gene is designated SEQ ID NO: 1 in the appended list of sequences (Appendix 2). The reading frame corresponding to the gene for the small subunit RR2 begins at position 1965 and ends at position 2759.

The RR2 sequence obtained exhibits a 54% homology at nucleotide level with the corresponding sequence of the VZV virus. This homology remains only 30% with the EBV virus, thereby showing again a greater homology of the sequences of the HVT virus with those of alphaherpesviruses.

EXAMPLE 2

INSERTION OF THE LacZ GENE INTO THE HVT VECTOR

The possibility of using the gene for the small subunit of ribonucleotide reductase as an insertion site for foreign genes may be demonstrated by substituting, in the first instance, a marker gene, for example the LacZ gene for beta-galactosidase, in its place.

If the site is indeed non-essential, the mutant virus HVT Lac RR2$\theta$, after in vivo recombination, will give a blue coloration in the presence of Xgal.

1 - Construction of a plasmid pHVT002 containing the lacZ gene in place of the gene for the small subunit of ribonucleotide reductase.

This plasmid was constructed in 3 steps:
introduction of a deletion in the gene for the small subunit of ribonucleotide reductase: plasmid pHVT 001;
creation of restriction sites by directed mutagenesis for the cloning of the heterologous gene; and
insertion of the lacZ gene for beta-galactosidase: plasmid pHVT 002.

Figure 2:
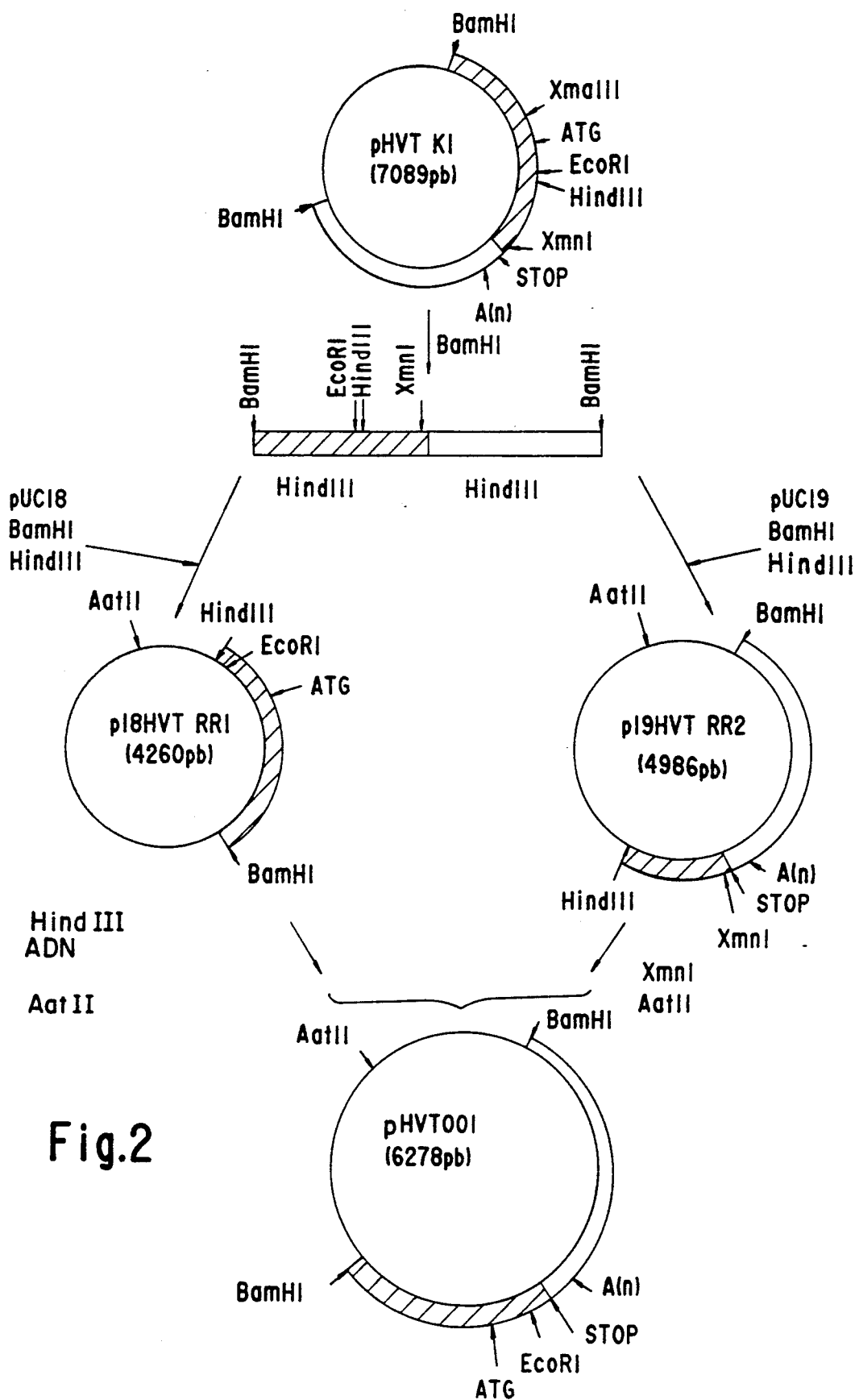
FIG. 2 shows a diagram explaining the introduction of a deletion in the small subunit RR2 of ribonucleotide reductase.

1.1 - Construction of plasmid pHVT001 (FIG. 2).

Plasmid pHVT K1, which contains the K1 BamHI restriction fragment, was digested with BamHI. This 4.2-kilobase fragment was purified by agarose gel electrophoresis. It was then digested with HindIII.

The 1374-base pair BamHI-HindIII fragment was subcloned into the vector pUC18, linearised beforehand, to give plasmid p18HVT RR1.

The 2826-base pair HindIII-BamHI fragment was subcloned into the vector pUC19 (38), linearised beforehand, to give plasmid p19HVT RR2.

Plasmid p18HVT RR1 was digested with HindIII. The ends of the DNA thus linearised were filled in by means of DNA polymerase (Klenow fragment). A second digestion with the enzyme AatII was then carried out. The 3578-base pair fragment having a blunt end and the other end corresponding to the AatII site was purified by agarose gel electrophoresis.

Plasmid p19HVT RR2 was digested with the restriction enzyme XmnI and then with the restriction enzyme AatII. The 2700-base pair AatII-XmnI restriction fragment, after purification on agarose gel, was ligated with the 3578-base pair fragment described in the previous paragraph to give plasmid pHVT001. This plasmid contains a deletion of 766 base pairs between the initial HindIII and XmnI sites.

Figure 3:
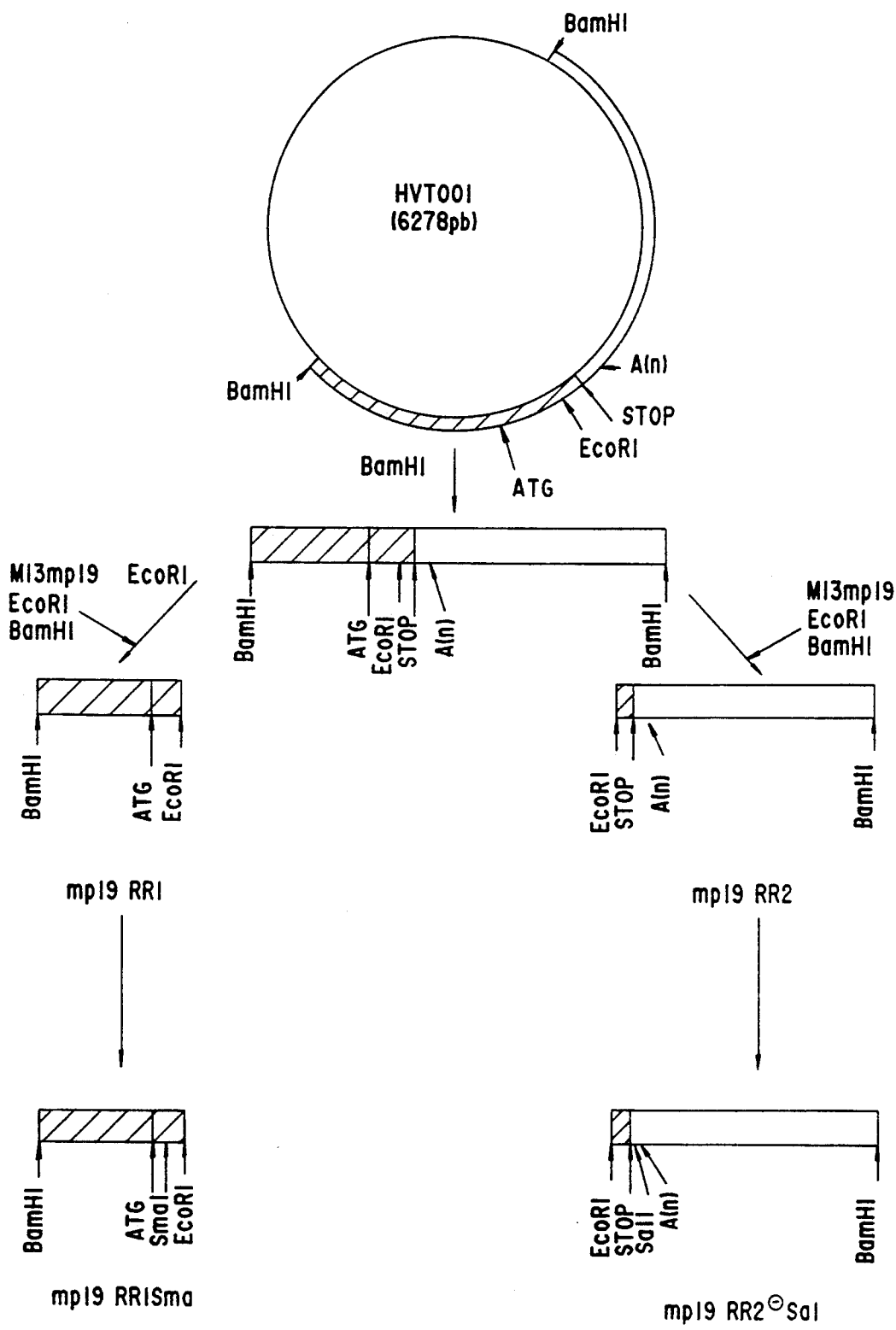
FIG. 3 shows a diagram explaining the creation of cloning sites by directed mutagenesis in the deleted gene for the small subunit RR2.

1.2 - Creation of cloning sites by directed mutagenesis (FIG. 3).

The 3440-base pair BamHI restriction fragment derived from plasmid pHVT001 was purified by electrophoresis and then digested with EcoRI. The 2 BamHI-EcoRI fragments, of respective sizes 1340 base pairs and 2100 base pairs approximately, were cloned into phage M13mp19 (38). The clones obtained are named mp19 RR1 and mp19 RR2$\theta$, respectively.

A SmaI site was created by directed mutagenesis in phage mp19 RR1, at the 3' end of the ATG, using the oligonucleotide designated SEQ ID NO: 3 in the appended list of sequences.

The phage thereby obtained is referred to as mp19 RR1 Sma.

A SalI site was introduced into phage mp19 RR2$\theta$ at the 5' end of the polyadenylation signal of the gene for the small subunit, using the oligonucleotide designated SEQ ID NO: 4.

The phage thereby obtained is referred to as mp19 RR2$\theta$ Sal.

Figure 4:
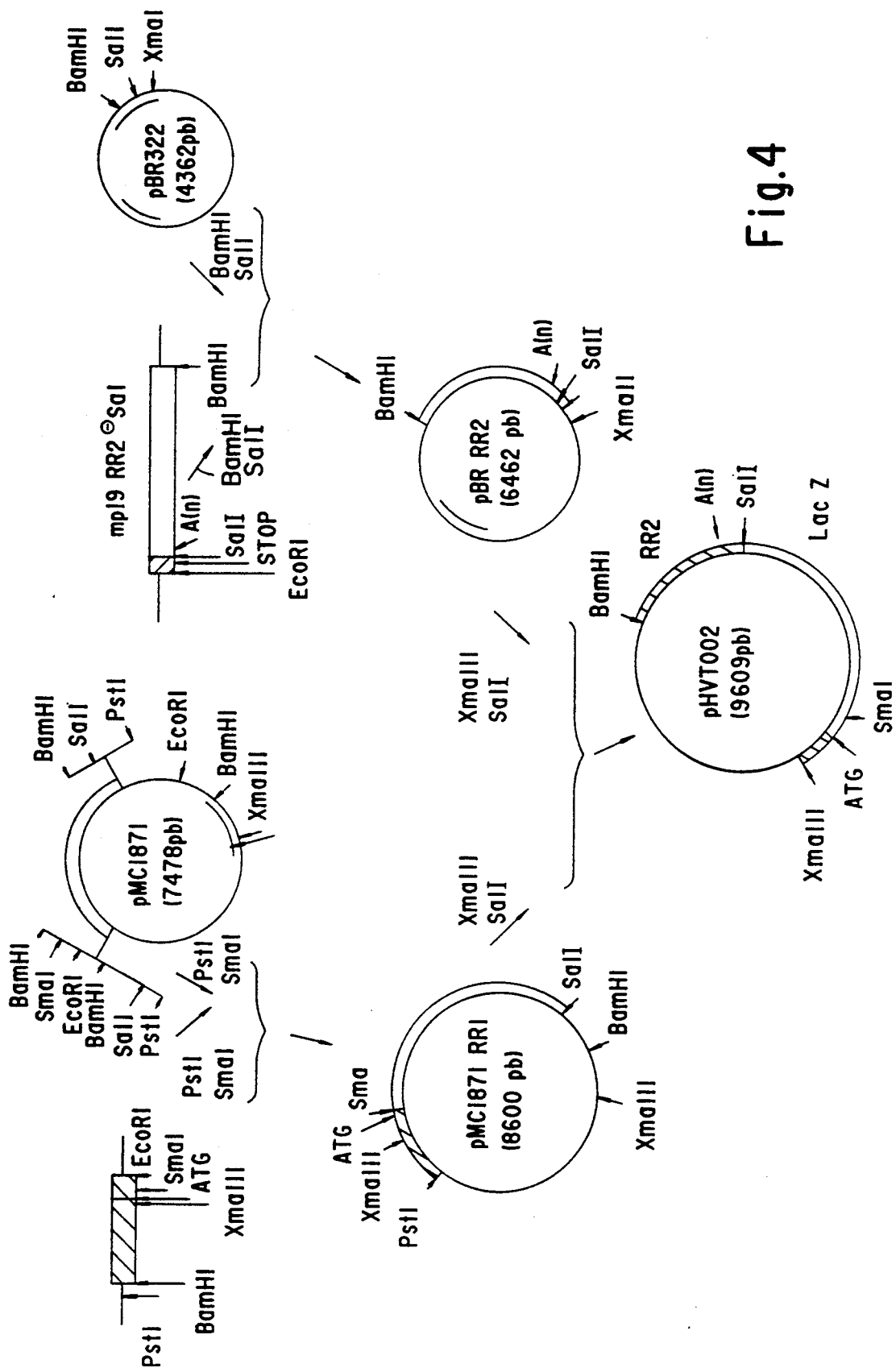
FIG. 4 shows a diagram explaining the insertion of the LacZ gene in place of the gene coding for the small subunit RR2 of ribonucleotide reductase.

1.3 - Creation of plasmid pHVT002 (FIG. 4).

The mutated 1340-base pair BamHI-EcoRI fragment contained in the vector mp19 RR1Sma, as described in FIG. 3, was purified by electrophoresis after digestion with PstI and SmaI. It was then cloned into the vector pMC1871 (Pharmacia-LKB, Uppsala, Sweden) (25) between the PstI and SmaI sites to give plasmid pMC1871 RR1.

This plasmid contains the 1,000 3'-terminal bases of the gene for the large subunit RR1 of ribonucleotide reductase and the LacZ gene in frame with the ATG of the small subunit RR2.

The approximately 2100-base pair mutated BamHI-EcoRI fragment originating from phage mp19 RR2$\theta$ Sal, as described in FIG. 3, was cloned into the vector pBR322 (37) between the BamHI and SalI sites to give plasmid pBR RR2$\theta$. The two new plasmids pMC1871 RR1 and pBR RR2$\theta$ were digested with XmaIII and SalI.

The 3665-base pair XmaIII-SalI fragment isolated from plasmid pMC1871 RR1 was purified by electrophoresis. In the same manner, the approximately 6200-base pair XmaIII-SalI fragment isolated from plasmid pBR RR2$\theta$ was purified. These two fragments were then ligated to give plasmid pHVT002.

This plasmid hence contains the 200 base pairs of the 3' portion of the RR1 gene, the 33 non-coding base pairs up to the ATG of the RR2 gene, then the LacZ gene inserted in frame and finally the non-coding 3' region of the RR2 gene.

2 - Production of a mutated HVT virus RR2$\theta$ LacZ

Primary chick embryo cells were cotransfected with 1 to 10 $\mu$g of plasmid pHVT002 and 1 $\mu$g of infectious HVT genomic DNA according to the Lipofectine technique. After 72 to 96 h of culture at 37° C. under a $CO_2$ atmosphere, numerous indications of a cytopathic effect were observed. The medium was then removed and replaced by an overlying layer of 1% agarose in F10-199 medium containing 0.5% of Xgal. Culturing was continued for 24 h. After 4 to 5 h, clearly identifiable blue plaques were obtained.

The cells were then withdrawn by punching out samples and extracting the latter, and the cell lawn remaining at the bottom of the well was taken up by adding one drop of trypsin. The whole was inoculated into healthy cells. A cytopathic effect was observed after 72 to 96 h. After the addition of Xgal, the infected cells exhibit blue-coloured lesions of the cell lawn.

EXAMPLE 3

INSERTION OF THE FUSION GENE OF NEWCASTLE DISEASE VIRUS

Insertion of the fusion gene of Newcastle disease virus was carried out in two steps:

1) Construction of plasmid pHVT003 comprising the deletion of the RR2 gene and the insertion of several cloning sites.

2) Construction of plasmid pHVT004 containing the fusion gene in place of the RR2 gene.

Figure 5:
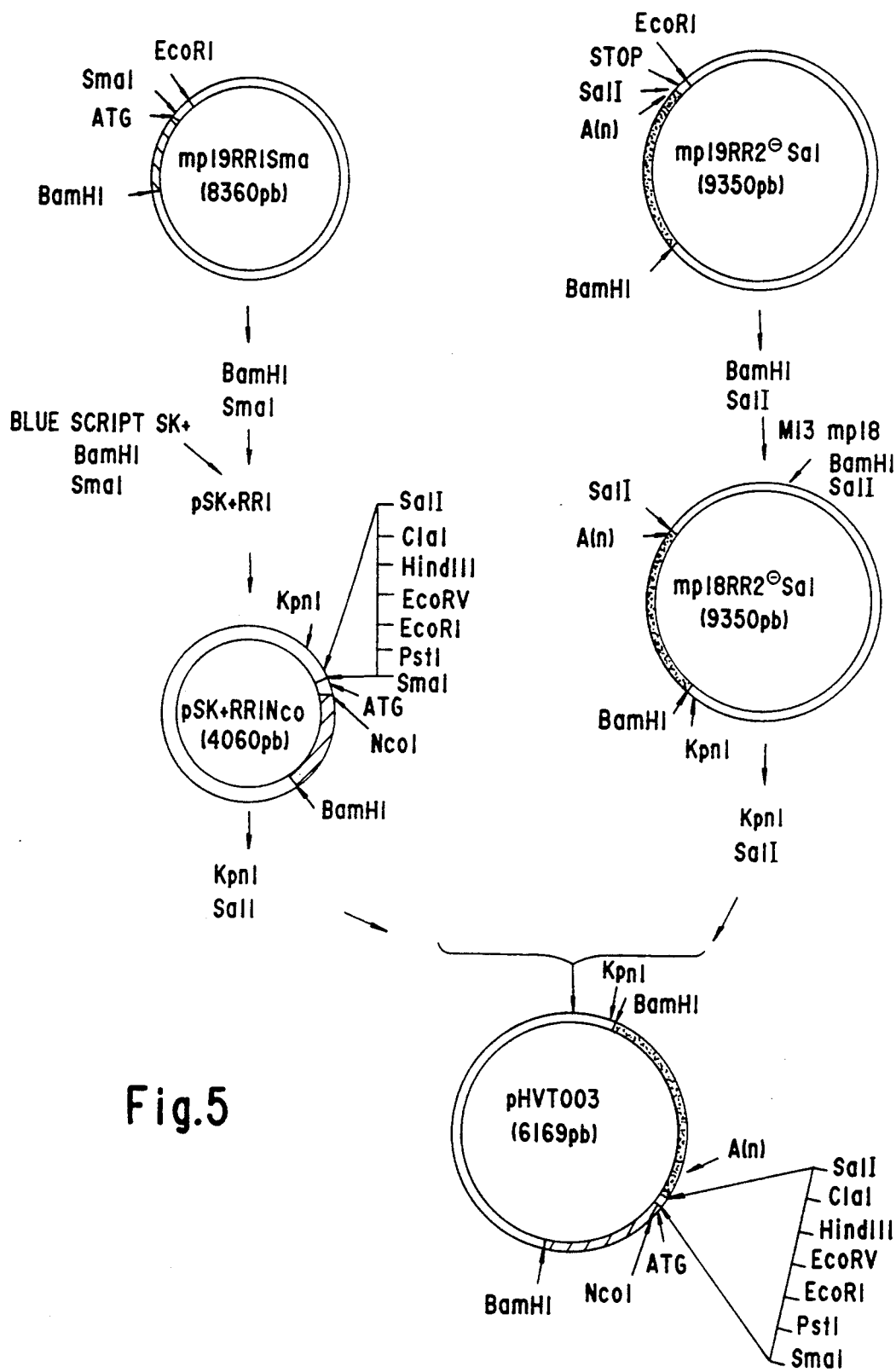
FIG. 5 shows a diagram explaining the introduction of a polylinker in place of the RR2 gene.
Figure 6:
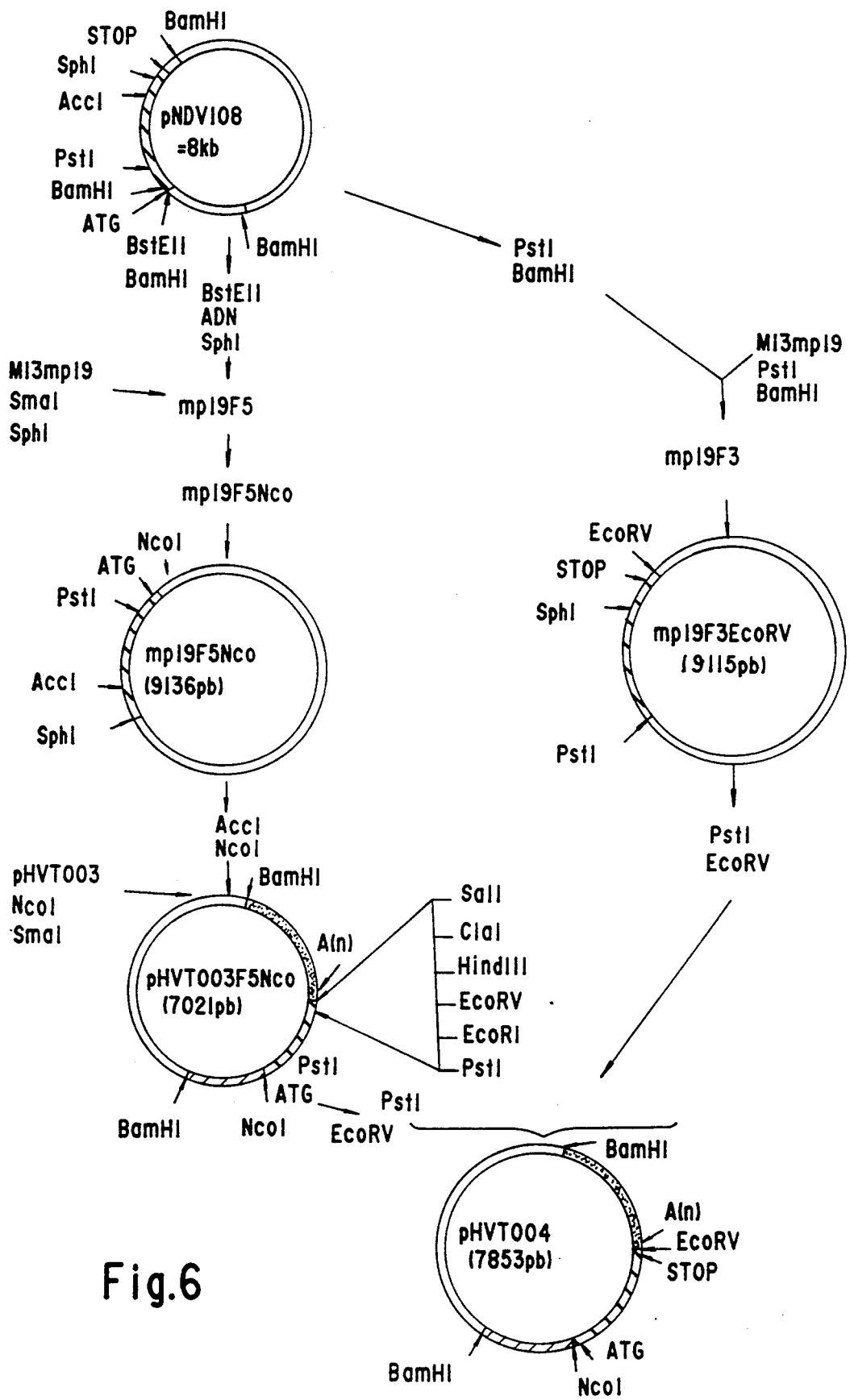
FIG. 6 shows a diagram explaining the insertion of the cDNA of the gene for the fusion protein of Newcastle disease virus.

1. Construction of plasmid pHVT003 (FIG. 5)

The mutated recombinant phage mp19 RR1Sma described in FIG. 3 was digested with SmaI and BamHI.

The 1110-base pair fragment liberated, which contains a portion of the RR1 gene and the ATG codon of the RR2 gene, was cloned into the vector Blue Script SK+ at the SmaI and BamHI restriction sites to give plasmid pSK+RR1. By directed mutagenesis, an NcoI restriction site was introduced at the ATG signal using the oligonucleotide SEQ ID NO: 5, thereby generating plasmid pSK+RR1Nco.

The mutated recombinant phage mp19 RR2θSal, described in FIG. 3, was digested with BamHI and SalI. The approximately 2.1-kilobase fragment liberated was cloned into the vector M13mp18 at the BamHI and SalI restriction sites. The clone obtained was referred to as mp18 RR2-Sal.

The approximately 2.1-kilobase fragment was liberated from phage mp18 RR2-Sal by KpnI and SalI digestion, and then introduced at these sites into plasmid pSK+RR1Nco, linearised with the enzymes KpnI and SalI. Plasmid pHVT003 was thereby constructed. It contains a portion of the RR1 gene, the non-coding 3' region of this gene, the ATG codon of the RR2 gene, a sequence comprising several single restriction sites and finally the non-coding 3' region of the RR2 gene.

2. Construction of plasmid pHVT004 which contains the fusion gene of Newcastle disease virus inserted in place of the RR2 gene.

The cDNA of the fusion gene was cloned into the vector pBR322 at the ScaI site, corresponding to plasmid pNDV108. The sequence of the fusion gene is given in the Appendix: SEQ ID NO: 2.

Plasmid pNDV108 was digested with BstEII and the ends filled in with DNA polymerase (Klenow fragment) and then with SphI. The 1786-base pair insert thus liberated was cloned into phage M13mp19, linearised with SmaI and SphI, to give phage mp19 F5. This phage is then mutagenised using the oligonucleotide SEQ ID NO: 6 to give the mutated phage mp19 F5Nco.

Phage mp19 F5Nco was digested with AccI and NcoI, and the 852-base pair fragment thereby obtained was cloned into the vector pHVT003, linearised with NcoI and SmaI, to give plasmid pHVT003 F5Nco.

This plasmid hence inserts the 3' terminal region of the RR1 gene, the 33 non-coding bases at the 3' end of this gene, then 852 bases of the fusion gene inserted in frame, a polylinker sequence and finally the non-coding region located at the 3' end of the RR2 gene.

Plasmid pNDV108 was digested with PstI and BamHI. The 1765-base pair fragment obtained was cloned into phage M13mp19, linearised with PstI and BamHI, to give phage mp19 F3, and then mutagenised using the oligonucleotide SEQ ID NO: 7 to give phage mp19 F5EcoRV. This phage was digested with PstI and EcoRV, and the 1567-base pair fragment thereby liberated was cloned into plasmid pHVT003 F5Nco, linearised with PstI and EcoRV, to give plasmid pHVT004.

This plasmid contains the 3' region of the RR1 gene, the 33 non-coding bases at the 3' end of this gene, then the fusion gene of Newcastle disease virus inserted in frame and finally the non-coding 3' region of the RR2 gene.

INSERTION OF THE FUSION GENE INTO THE HVT VECTOR VIRUS

Plasmid pHVT004 was used in experiments of co-transfection of chick embryo fibroblast cells with infectious DNA of the HVT virus. A recombinant HVT virus expressing the fusion gene of Newcastle disease virus can thereby be obtained.

The small subunit of ribonucleotide reductase may hence be used for inserting genes into the genome of HVT virus, and the promoters of ribonucleotide reductase are effective for permitting their expression.

Genes coding for immunogens associated with Marek's disease, infectious avian bronchitis, Newcastle disease, fowl plague, Gumboro disease, avian anaemia, egg drop syndrome, coccidiosis, fowlpox, infectious rhinotracheitis, colibacillosis, pasteurellosis or haemophilosis can thus be inserted.

The recombinant viruses thereby obtained may be used as vectors for expression of the inserted gene, in vaccines known as chimeric vaccines. The permanent viremia for which the HVT virus is responsible should enable the immunogens expressed to be well disseminated, and thereby induce the desired immune response.

Although the process has been described in relation to the HVT virus, it will be understood that it is sufficient, in particular, to adapt the restriction enzymes in order to extrapolate this process to other non-pathogenic and non-oncogenic herpesviruses, or herpesviruses rendered non-pathogenic and non-oncogenic, and thus to propose vaccines employing recombinant viruses for man and other animal species.

Naturally, the recombinant viruses according to the invention can then contain, in addition to the gene or genes inserted into the gene for the small subunit RR2, one or more genes inserted at other points of the genome, for example into the large subunit RR1 or into the gene coding for thymidine kinase.

APPENDIX 1: BIBLIOGRAPHIC INDEX

1. A. E. BUCKMASTER, S. D. SCOTT, M. J. SANDERSEN, M. E. G. BOURSNELL, L. J. N. ROSS and M. H. BINNS (1988), J. Gen. Virol., 69, 2033-2042
2. P. L. FELGNER, T. R. GADEK, M. HOLM, R. ROMAN, H. W. CHAN, M. WENZ, J. P. NORTHROP, G. M. RINGOLD and M. DANIELSEN (1987), Proc. Natl. Acad. Sci., USA, 84, 7413
3. H. FIELD and P. WILDY (1987), J. Hygiene (Cambridge), 81, 267-277
4. D. J. GOLDSTEIN and S. K. WELLER (1988), J. Virol., 62, 196-205
5. D. J. GOLDSTEIN and S. K. WELLER (1988), Virology, 166, 41-51
6. J. GOUGH and N. MURRAY (1983), J. Mol. Biol., 166, 1-19
7. J. G. JACOBSON, D. A. LEIB, D. J. GOLDSTEIN, C. L. BOGART, P. A. SCHAFFER, S. K.

WELLER and D. M. COEN (1989), Virology, 173 (1), 276-283
8. A. T. JAMIESON et al. (1974), J. Gen. Virol., 24, 465-480
9. EP-A-0,316,658
10. T. KUNKEL (1985), Proc. Natl. Acad. Sci., 82, 488-492
11. T. KUNKEL, J. ROBERTS and B. ZAKOUR (1987), In Methods in Enzymology, 154, 367-382 Acad. Press
12. Y. LANGELIER and G. BUTTIN (1981), J. Gen. Virol., 57, 21-31
13. H. LANKINEN, A. GAASLUND and L. THELANDER (1982), J. Virol., 41, 893-900
14. LEE et al. (1980), J. Gen. Virol., 51, 245-253
15. J. McLAUCHLAN and J. B. CLEMENTS (1983), The Embo Journal, 2, (11), 1953-1961
16. J. McLAUCHLAN and J. B. CLEMENTS (1983), J. Gen. Virol., 64, 997-1006
17. T. MANIATIS, E. F. FRITSCH and J. SAMBROOK (1982), "Molecular cloning: A laboratory manual" Cold Spring Harbor Laboratory, Cold Spring Harbor, N.Y.
18. C. T. METTENLEITER, C. SCHREURS, F. ZUCKERMANN and T. BEN PORAT (1987), J. Virol., 61, 4030-4032
19. K. NAKAMAYE and F. ECKSTEIN (1985), Nucleic Acid Res., 13, 9679-9698
20. V. G. PRESTON, A. J. DARLING and I. M. McDOUGALL (1988), Virology, 167, 458-467
21. B. ROIZMAN et al. (1983), Cold Spring Harbor Conference on New Approaches to Viral Vaccines, September 1983
22. M. RUSSEL, S. KIDD and M. KELLEY (1986), Gene, 45, 333-338
23. P. J. SANDERS (1982), J. Gen. Virol., 63, 277-295
24. F. SANGER, S. NICKLEN and A. R. COULSON (1977), Proc. Natl. Acad., USA, 74, 5463-5467
25. S. K. SHAPIRA et al. (1983), Gene, 25, 71-82
26. M. F. SHIH, M. ARSENAKIS, P. THIOLLAIS and B. ROIZMAN (1984), Proc. Natl. Acad. Sci., USA, 81, 5867-5870
27. S. SIMPSON, J. McLAUCHLAN and J. B. CLEMENTS (1989), 14th International Herpesvirus Workshop, Nyborgstrand, Denmark (1989)
28. M. A. SWAIN and D. A. GALLOWAY (1986), J. Virol., 57, (3), 802-808
29. S. TABOR and C. C. RICHARDSON (1987), Proc. Natl. Acad. Sci., USA, 84, No. 14, 4767-4771
30. G. TATAROV (1968), Zentralbl. Vet. Med., 15B, 848-853
31. J. W. TAYLOR et al. (1985), Nucleic Acid Res., 13, 8749-8764
32. J. W TAYLOR, J. OTT and F. ECKSTEIN (1985), Nucleic Acid Res., 13, 8764-8785
33. R. L. THOMPSON, E. K. WAGNER and J. G. STEVENS (1983), Virology, 131, 180-192
34. D. R. THOMSEN, C. C. MARCHIOLI and R. J. YANCEY (1987), J. Virol., 61, 229-232
35. P. C. WEBER (1987), Science, 236, 576-579
36. R. L. WITTER et al. (1970), Am. J. Vet. Res., 31, 525-538
37. BOLIVAR F. et al., Gene 1977, 2, 95-113
38. YANNISCH-PERRON C. et al., Gene 1985, 33, 103-119.

---

We claim:

1. Recombinant HVT comprising at least one heterologous gene inserted into the region of the genome of said virus corresponding to the gene for the small subunit RR2 of ribonucleotide reductase, so as to be capable of being expressed.

2. Recombinant virus according to claim 1, characterised in that the heterologous gene codes for a viral, bacterial or parasitic antigen.

3. Recombinant HVT virus according to claim 2 wherein the antigen is a component of a pathogenic agent of a disease selected from the group consisting of Marek's disease, infectious avian bronchitis, Newcastle disease, fowl plague, Gumboro disease, avian anaemia, egg drop syndrome, fowlpox, infectious laryngotracheitis, coccidiosis, colibacillosis, pasteurellosis and haemophilosis.

4. Recombinant virus according to claim 2, characterised in that the inserted heterologous gene is capable of being expressed under the control of the transcription regulation sequences of the gene for the small subunit RR2.

5. Recombinant virus according to claim 2, characterised in that the inserted heterologous gene is capable of being expressed under the control of endogenous promoter sequences from said virus or of exogenous herpesvirus promoter sequences which are transferred to the genome of the virus in question.

6. Recombinant virus according to claim 2, characterised in that the initiation and termination codons of the RR2 gene are replaced by those of the gene to be inserted.

7. Process for preparing a recombinant virus from a HVT characterised in that at least one heterologous gene is inserted into the region of the genome of said virus which corresponds to the gene for the small subunit RR2 of ribonucleotide reductase, in such a way that said heterologous gene can be expressed.

8. Process according to claim 7, characterized in that a portion of the viral genome sufficient to promote homologous recombination with the HVT genome and containing the gene for the small subunit RR2 is isolated, a partial or total deletion of this gene is carried out and the heterologous gene is inserted into the region corresponding to said gene before inserting the DNA sequence obtained into the genome of the virus by cotransfection into recipient host cells and homologous recombination in said cell.

9. Process according to claim 7, characterised in that the inserted gene is under the control of transcription regulation sequences of the RR2 gene.

10. Process according to claim 7, characterised in that the inserted gene is under the control of endogenous HVT promoter sequences or exogenous herpesvirus promoter sequences which are transferred to the genome of the virus in question.

11. Process according to claim 7 characterised in that the initiation and termination codons of the RR2 gene are replaced by those of the gene to be inserted.

12. Process for preparing a recombinant HVT, characterised in that:
a) a K1 Bam HI fragment of the HVT genome is isolated by digestion of the genome with the restriction enzyme Bam HI,
b) this fragment is digested with the restriction enzyme Hind III, to obtain a fragment corresponding to the 5' portion of the RR2 gene and to the region upstream including the promoter, and a fragment corresponding to the 3' portion of the RR2 gene and to the region downstream of this gene,
c) the two fragments, 5' and 3', obtained in b) are cloned, respectively, into the vectors pUC18 and pUC19,
d) these plasmids are digested, respectively, with the restriction enzyme systems Hind III/Aat II and Xmn I/Aat II and then ligated together to give a new plasmid containing a deletion between the initial Hind III and Xmn I sites,
e) restriction sites are created by directed mutagenesis in the plasmid obtained in d),
f) a heterologous gene is cloned into these restriction sites, and
g) the DNA fragment obtained in f) is inserted into the genome of the HVT virus by cotransfection and homologous recombination.

13. Process according to claim 12, characterised in that the heterologous gene codes for an immunogen originating from pathogenic agents associated with an avian disease.

14. Recombinant virus obtained according to claim 7.

15. Vaccine comprising a recombinant virus according to claim 1.

16. Nucleotide sequence designated SEQ ID NO: 1 corresponding to the gene for the small subunit RR2 of ribonucleotide reductase of the HVT or a fragment of said sequence wherein said fragment encodes a polypeptide characterized by the antigenicity of the small subunit RR2 of ribonucleotide reductase of the HVT virus.

17. Process according to claim 13 wherein the disease is selected from the group consisting of Marek's disease, infectious avian bronchitis, Newcastle disease, fowl plague, Gumboro disease, avian anaemia, egg drop syndrome, fowlpox, infectious laryngotracheitis, coccidiosis, colibacillosis, pasteurellosis and haemophilosis.

* * * * *